(12) United States Patent
Koehler et al.

(10) Patent No.: US 9,775,335 B2
(45) Date of Patent: Oct. 3, 2017

(54) DURABLE COATING-EMBEDDED PESTICIDES WITH PEEL AND STICK MOSQUITO TREATMENT OF CONTAINERS

(71) Applicant: University of Florida Research Foundation, Inc., Gainesville, FL (US)

(72) Inventors: Philip G. Koehler, Gainesville, FL (US); Roberto M. Pereira, Gainesville, FL (US); Enrico Paolo Levi, London (GB)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/367,874

(22) Filed: Dec. 2, 2016

(65) Prior Publication Data

US 2017/0105402 A1 Apr. 20, 2017

Related U.S. Application Data

(60) Continuation-in-part of application No. 15/048,604, filed on Feb. 19, 2016, now Pat. No. 9,572,338, which (Continued)

(51) Int. Cl.
*A01M 1/20* (2006.01)
*A01M 1/02* (2006.01)

(Continued)

(52) U.S. Cl.
CPC ............... *A01M 1/20* (2013.01); *A01M 1/02* (2013.01); *A01M 1/106* (2013.01); *A01N 25/08* (2013.01)

(58) Field of Classification Search
CPC ............ A01M 1/00; A01M 1/02; A01M 1/10; A01M 1/106; A01M 1/20; A01M 1/2005; A01M 1/2016

(Continued)

(56) References Cited

U.S. PATENT DOCUMENTS

| 4,103,450 A | 8/1978 | Whitcomb |
| 4,218,843 A | 8/1980 | Clarke, Jr. |

(Continued)

FOREIGN PATENT DOCUMENTS

| EP | 2084963 | 8/2009 |
| WO | 03081119 | 10/2003 |

(Continued)

OTHER PUBLICATIONS

Tikasingh, et al., A Multi-Paddle Ovitrap for Collecting Haemagogus and Aedes Aegypti Eggs, Moquito News, 1983, pp. 358-360, vol. 43, No. 3.

(Continued)

*Primary Examiner* — Richard G Davis
(74) *Attorney, Agent, or Firm* — Brian S. Steinberger; Law Offices of Brian S. Steinberger, P.A.

(57) ABSTRACT

Water-holding vessels and containers, such as flower pots, water holding dishes used under plant pots, vases, bird baths, and fountains and storm water inlets, can be coated with novel larvicide and/or adulticide coatings. Small objects can be coated with imbedded larvicide or larvicide and adulticide combination, which can be dropped in water-holding containers which can leach out pesticide over time which prevents mosquitoes from breeding in the water-holding containers. The small objects can be on the adhesive side of peel and stick type tape to form a peel and stick mosquitocidal chip (PSMC), which can be applied to the inner sides and/or bottoms of vessels/containers that can be exposed to water. A tape type roll can include an upper protective layer that protects a coating on a strip, the coating being a polymer coating having imbedded pesticide with or without silica. Under the strip can be an adhesive surface that is protected by a removable lower protective layer. Removing the lower (Continued)

protective layer can allow for the strip to be applied to water exposed surfaces for the treatment of mosquitoes.

18 Claims, 29 Drawing Sheets

Related U.S. Application Data is a division of application No. 14/204,524, filed on Mar. 11, 2014, now Pat. No. 9,295,246.

(60) Provisional application No. 61/777,766, filed on Mar. 12, 2013.

(51) Int. Cl.
*A01M 1/10* (2006.01)
*A01N 25/08* (2006.01)

(58) Field of Classification Search
USPC .................................... 43/107, 132.1, 133
See application file for complete search history.

(56) References Cited

U.S. PATENT DOCUMENTS

| | | | |
|---|---|---|---|
| 4,631,857 A | 12/1986 | Kase et al. | |
| 4,671,010 A | 6/1987 | Conlee et al. | |
| 4,971,796 A | 11/1990 | Sjogren | |
| 4,977,701 A | 12/1990 | Sherman | |
| 5,401,310 A | 3/1995 | Ture | |
| 5,698,210 A * | 12/1997 | Levy | A01N 25/10 424/405 |
| 5,775,026 A | 7/1998 | Pearce et al. | |
| 5,776,353 A | 7/1998 | Palm et al. | |
| 5,983,557 A * | 11/1999 | Perich | A01M 1/04 43/107 |
| 5,987,809 A | 11/1999 | Cheok | |
| 6,185,861 B1 | 2/2001 | Perich et al. | |
| 6,389,740 B2 | 5/2002 | Perich et al. | |
| 7,763,083 B2 | 7/2010 | Kimball et al. | |
| 7,837,988 B2 | 11/2010 | Sjogren et al. | |
| 8,343,524 B2 | 1/2013 | Willis et al. | |
| 9,192,151 B2 | 11/2015 | Koehler et al. | |
| 9,295,246 B2 | 3/2016 | Koehler et al. | |
| 9,351,494 B2 | 5/2016 | Woods et al. | |
| 2002/0116899 A1 * | 8/2002 | Weder | A01G 5/04 53/397 |
| 2005/0081428 A1 | 4/2005 | Ramsey et al. | |
| 2005/0160659 A1 | 7/2005 | Forehand | |
| 2007/0232497 A1 * | 10/2007 | Chew | A01N 25/34 504/360 |
| 2008/0028669 A1 * | 2/2008 | Hurwitz | A01M 1/14 43/114 |
| 2008/0115406 A1 * | 5/2008 | Duston | A01M 29/34 43/131 |
| 2010/0043276 A1 | 2/2010 | Eger, Jr. et al. | |
| 2010/0132245 A1 | 6/2010 | Vestergaard Frandsen | |
| 2010/0158965 A1 * | 6/2010 | Beitzel | A01N 25/34 424/405 |
| 2011/0094581 A1 | 4/2011 | Sawada et al. | |
| 2011/0145667 A1 | 6/2011 | Whetsel | |
| 2011/0289824 A1 | 12/2011 | Wu et al. | |
| 2012/0280055 A1 * | 11/2012 | Schneidmiller | A01M 1/02 239/6 |
| 2013/0067795 A1 | 3/2013 | Wesson et al. | |
| 2013/0276355 A1 | 10/2013 | Koehler et al. | |
| 2015/0020438 A1 * | 1/2015 | Work | A01M 1/14 43/114 |

FOREIGN PATENT DOCUMENTS

| | | |
|---|---|---|
| WO | 2004030453 | 4/2004 |
| WO | 2005107470 | 11/2005 |
| WO | 2006111692 | 10/2006 |
| WO | 2011094581 | 8/2011 |
| WO | 2011145667 | 11/2011 |
| WO | 2012056191 | 5/2012 |
| WO | 2014028835 | 2/2014 |

OTHER PUBLICATIONS

Kloter, et al., Evaluation of Some Ovitrap Materials Using for Aedes Aegypti Surveillance, Mosquito News, 1983, pp. 438-439, vol. 43, No. 4.
Ikeshoji, et al., Surfactants for a Mosquito Ovitrap, Jap. J. Sanit. Zool., pp. 451-452. vol. 28, No. 4.
Mogi, et al., Ovitrap Surveys of Dengue Vector Mosquitoes in Chiang Mai, Northern Thailand: Seasonal Shifts in Relative Abundance of Aedes Albopictus and Ae.aegypti, Medical and Veterinary Entomology, 1988, pp. 319-324, Vol. 2.
Zeichner, The Lethal Ovitrap: A Response to the Resurgence of Dengue and Chikungunya, U.S. Army Medical Department Journal, 2011, retrieved from http://findarticles.com/p/atricles/mi_m0VVY/is_2011_July-Sept/ai_n58163605/pg_4/, 3 pages.
Refrasud International s.r.l. refractory innovation technology, Carbonxide 010/LP, Jun. 2012, S.S. 172 per Martina F., s.n.—74100, Taranto—Italy, 1 page.
Koehler, et al., PCT Application No. PCT/US2014/023478 filed Mar. 11, 2014, Notification Concerning Transmittal of International Preliminary Report on Patentability (Chapter I of the Patent Cooperation Treaty), mailed Sep. 24, 215, 12 pages.
University of Florida Research Foundation, Inc., Dual Action Lethal Containers and Compositions for Killing Adult Mosquitos and Larvae, European patent application No. 13778229.8-1656 European Search Report mailed Jun. 2, 2015, 7 pages.
University of Florida Research Foundation, Inc., et al., PCT Application No. PCT/US13/37422 filed Apr. 19, 2013, Notification of Transmittal of the International Search Report and the Written Opinion of the International Searching Authority, or the Declaration mailed Jul. 31, 2013, 13 pages.
University of Florida Research Foundation, Inc., PCT Application No. PCT/US14/23478 filed Mar. 11, 2014, Notification of Transmittal of the International Search Report and the Written Opinion of the International Searching Authority, or the Declaration mailed Jul. 24, 2014, 15 pages.
University of Florida Research Foundation, Inc., European Patent Application No. 14779603.1-1656, Mosquito Control Devices Using Durable Coating Embedded Pesticides, Notification of EPO Search Report dated Oct. 10, 2016, 9 pages.
The Betty Mills Company, Inner Health Mosquito No Bite Patches—6 Pack—Inner Health 1113984, retrieved from http://www.bettymills.com/mosquito-no-bite-patches-6-pack-inner-health-1113984?referer=search on Nov. 15, 2016, 4 pages.

* cited by examiner

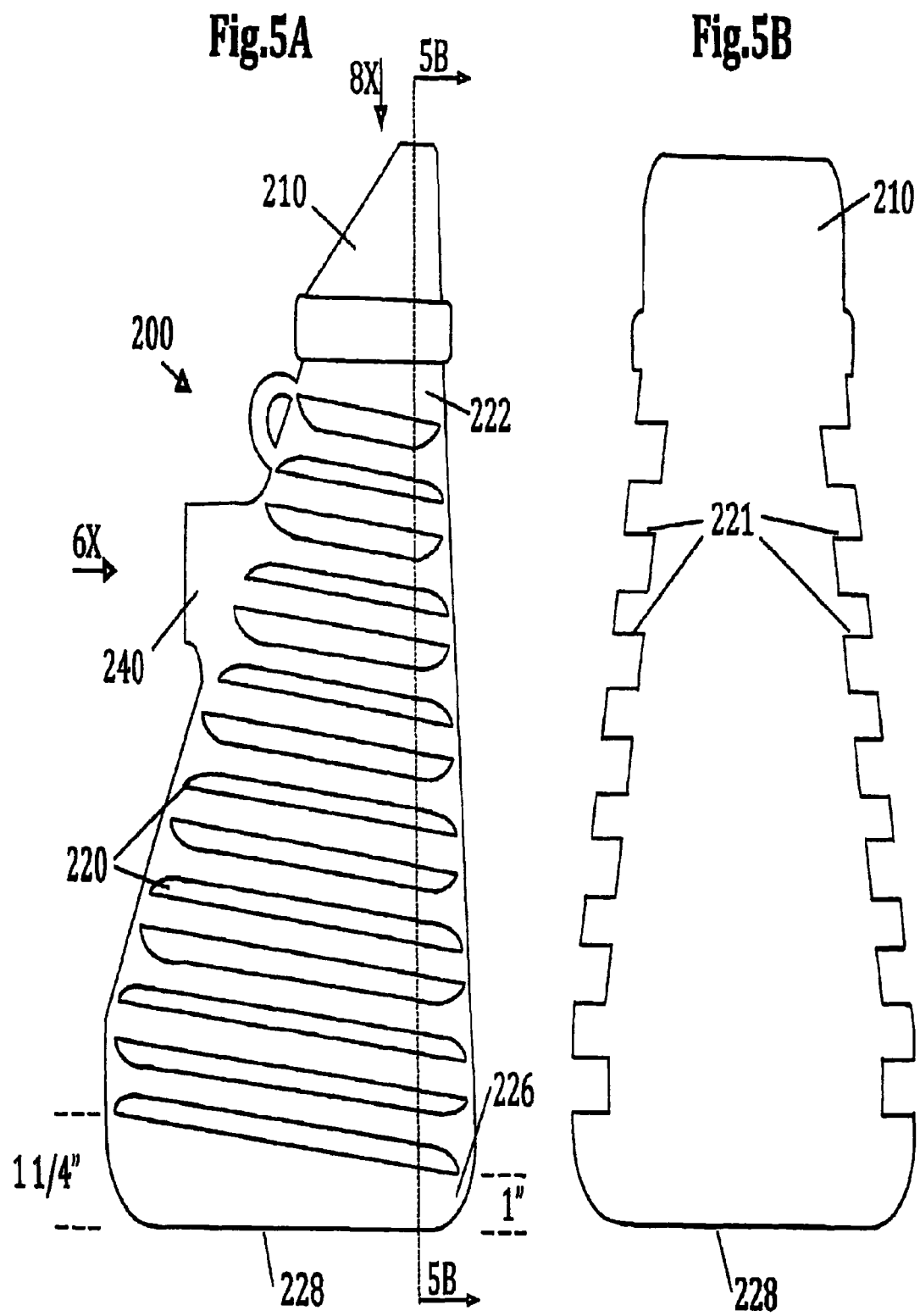

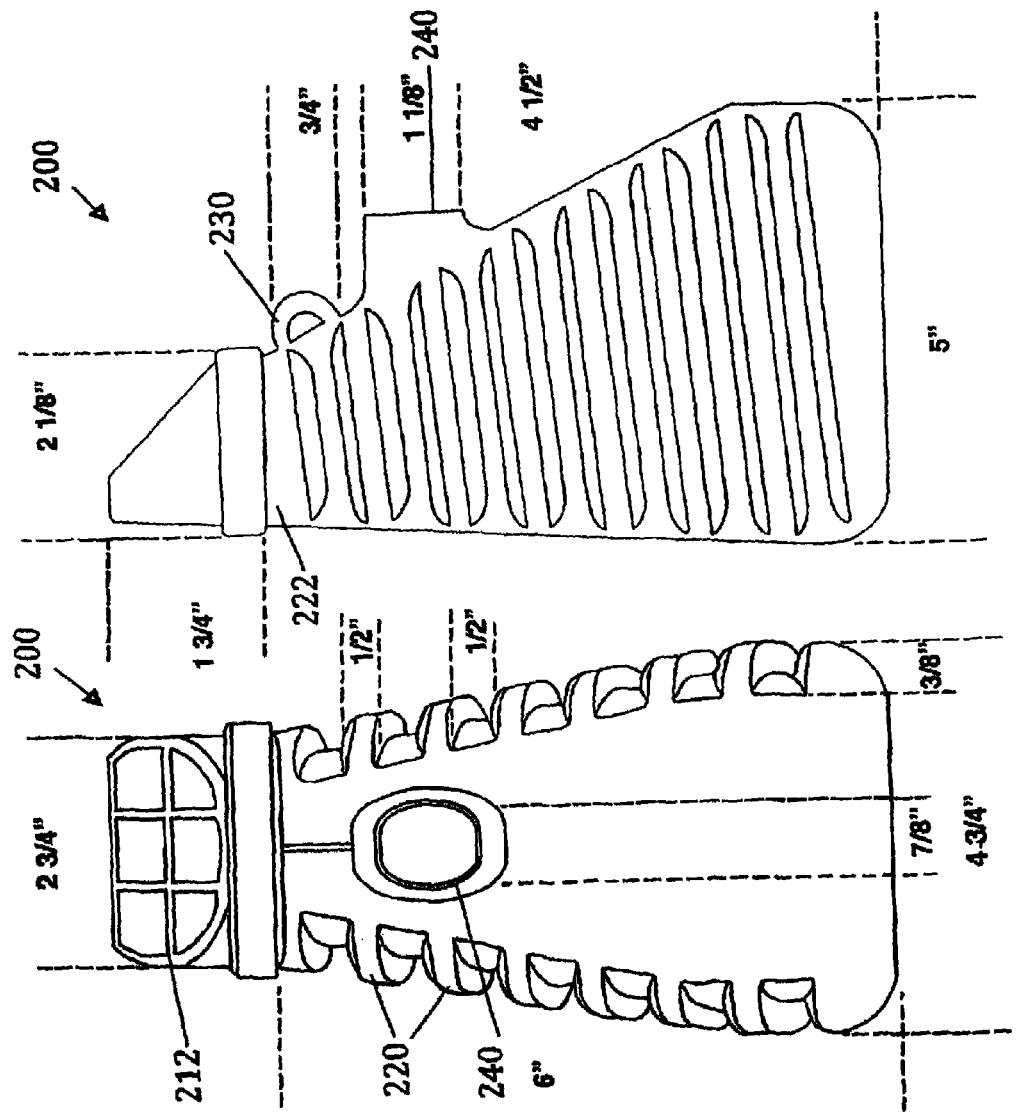

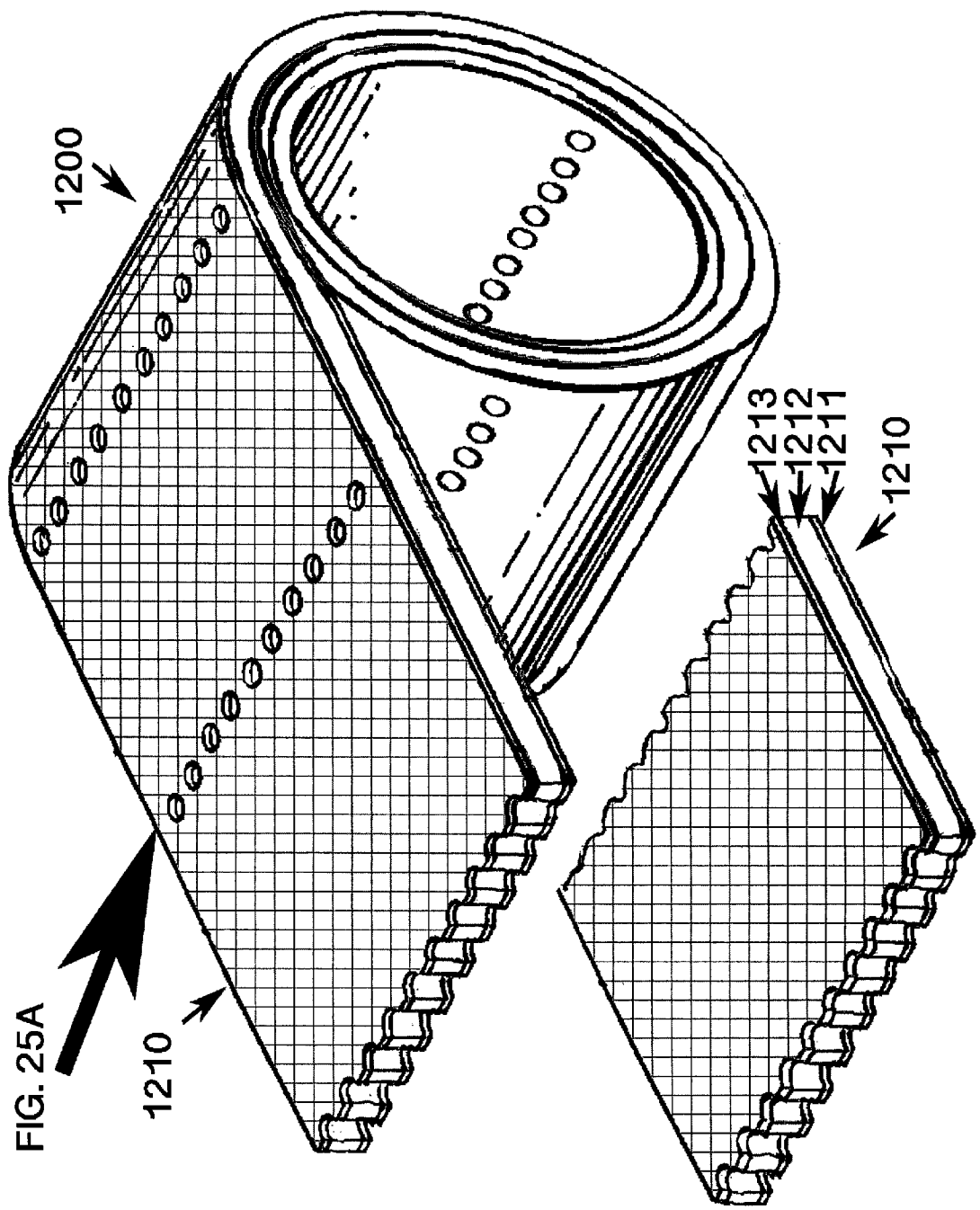

Cross-Section of Peel-and-Stick Larvicidal Sticker/Chip – Prior to application
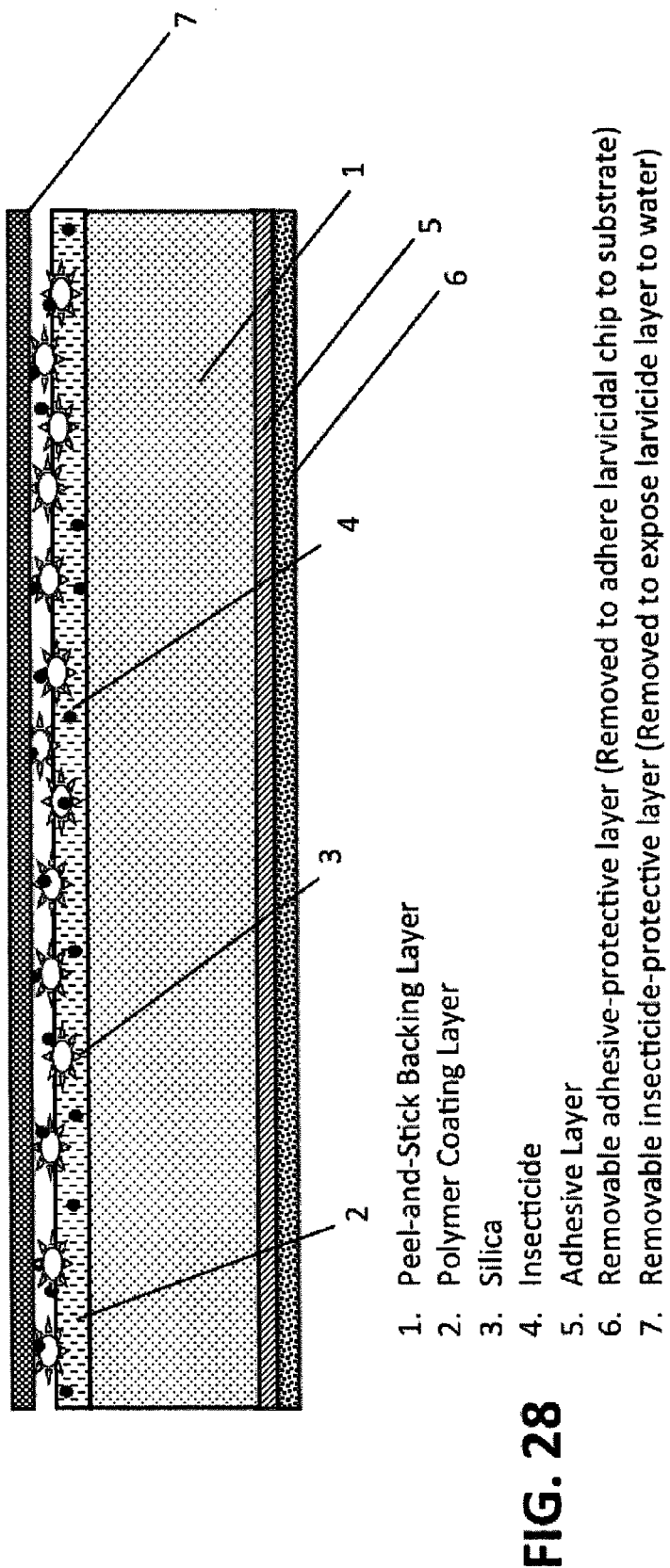
1. Peel-and-Stick Backing Layer
2. Polymer Coating Layer
3. Silica
4. Insecticide
5. Adhesive Layer
6. Removable adhesive-protective layer (Removed to adhere larvicidal chip to substrate)
7. Removable insecticide-protective layer (Removed to expose larvicide layer to water

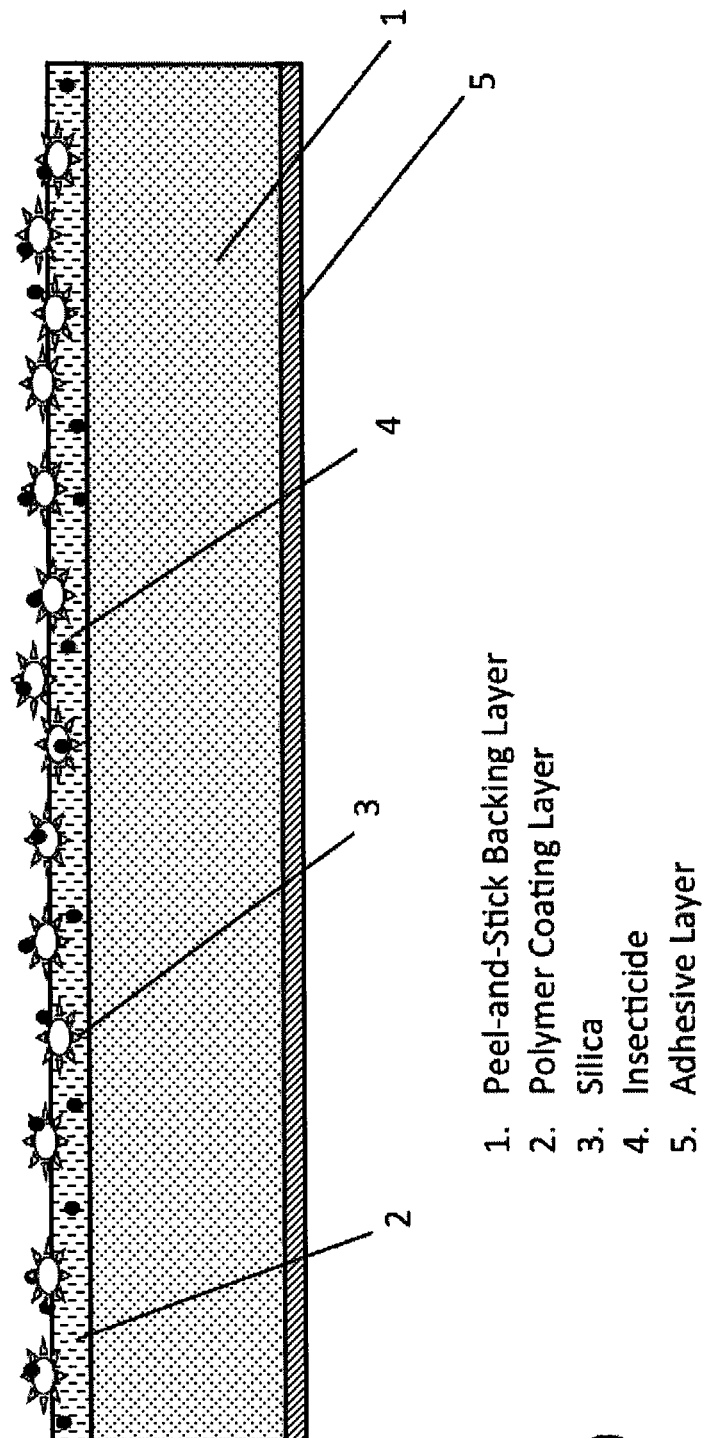

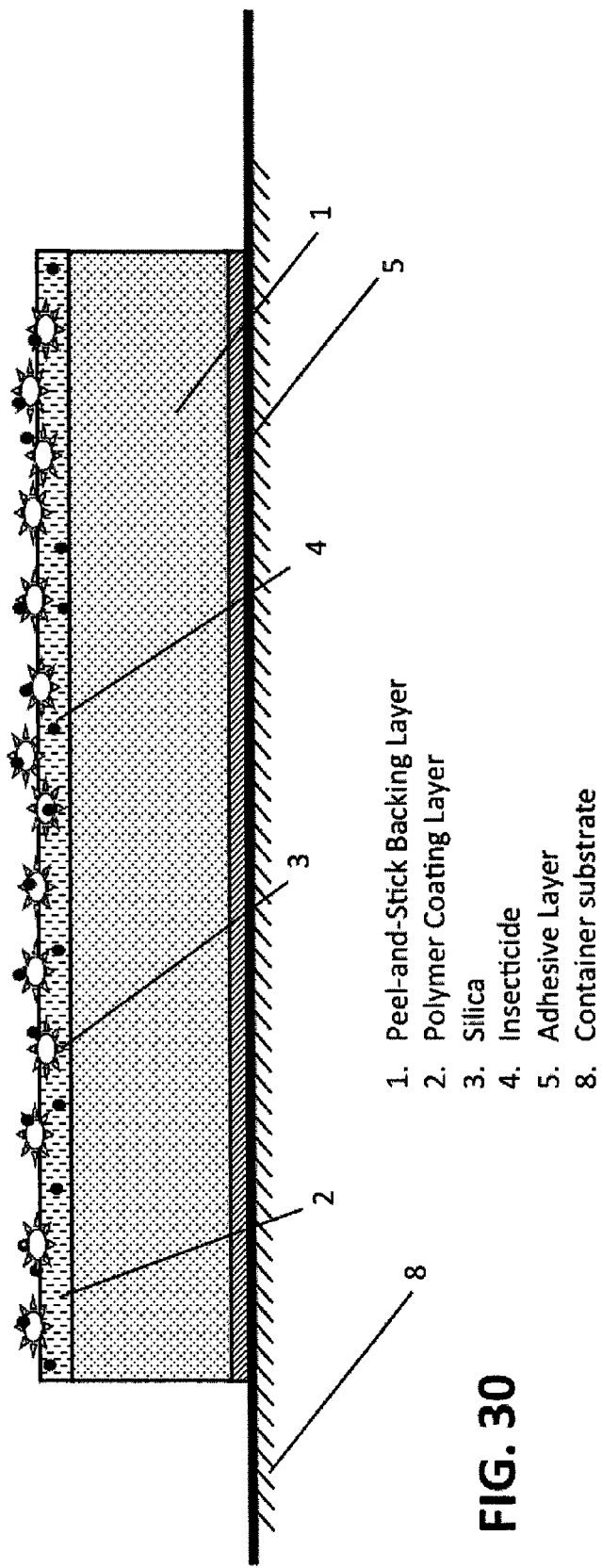

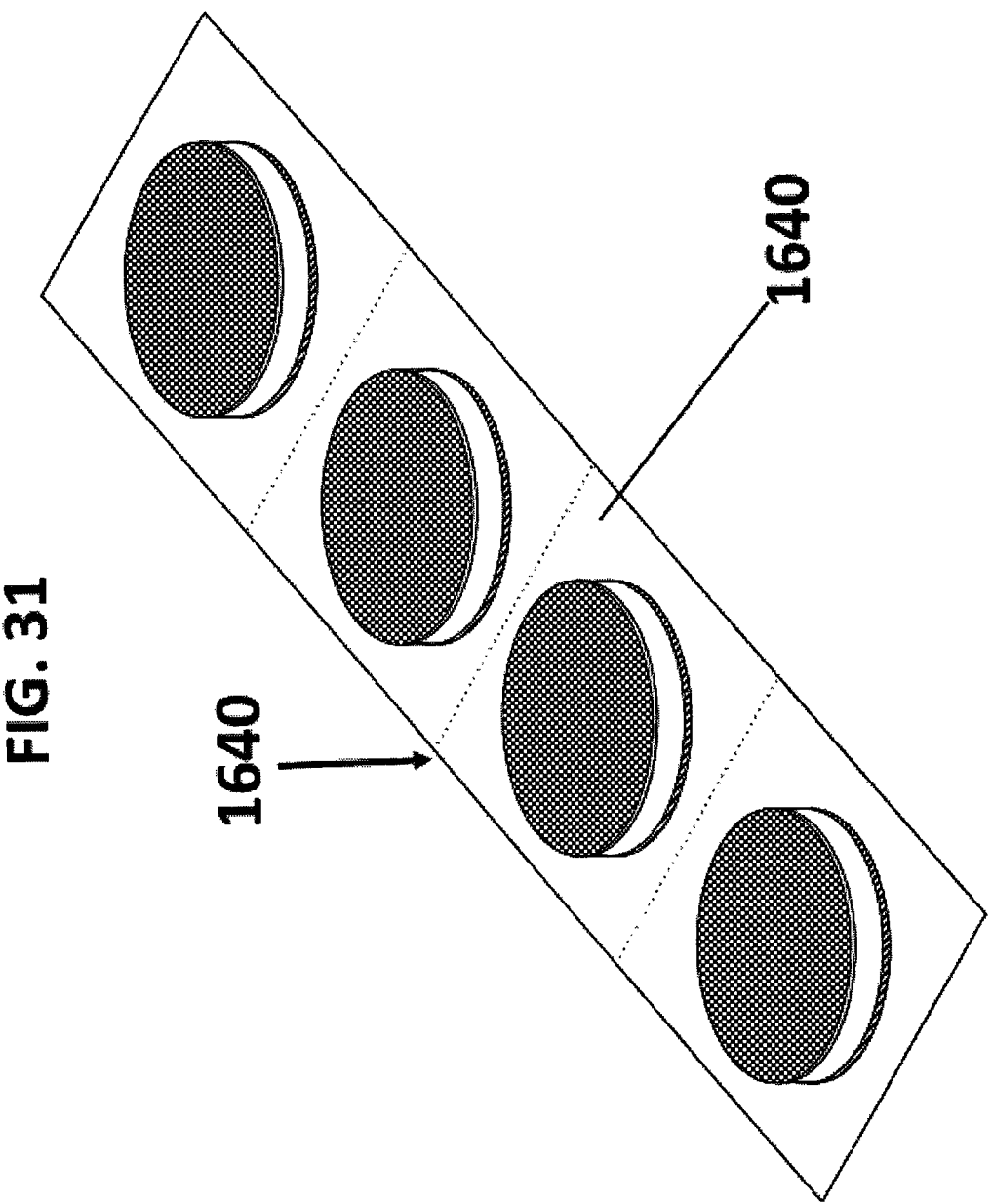

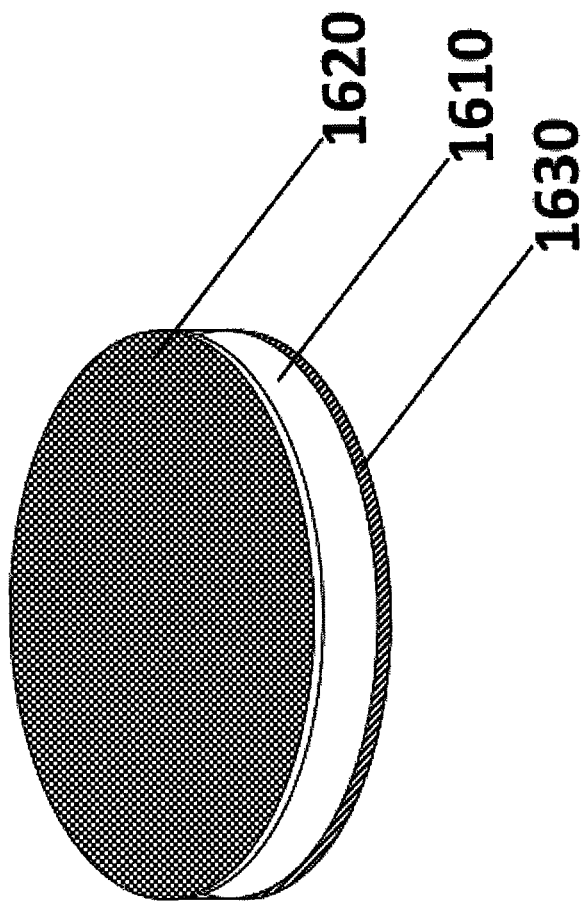

DURABLE COATING-EMBEDDED PESTICIDES WITH PEEL AND STICK MOSQUITO TREATMENT OF CONTAINERS

CROSS REFERENCE TO RELATED APPLICATION

This application is a Continuation-In-Part of U.S. patent application Ser. No. 15/048,604 filed Feb. 19, 2016, now U.S. Pat. No. 9,572,338, which is a Divisional of U.S. patent application Ser. No. 14/204,524 filed Mar. 11, 2014, now U.S. Pat. No. 9,295,246, which claims the benefit of priority to U.S. Provisional Application Ser. No. 61/777,766 filed Mar. 12, 2013. The entire disclosure of each of the applications listed in this paragraph are incorporated herein by specific reference thereto.

GOVERNMENT LICENSE RIGHTS

This invention was made with Government support under Dept. of Agriculture-Agricultural Research Service Agreement No.: 58-0208-3-001 (Durable Coating-Embedded Adulticide (CEA), Larvicide (CEL) and Durable Dual-Action Lethal Ovitraps (DDALO) for Management of Dengue Vector *Aedes albopictus* and Other Container-Breeding Mosquitoes). The government has certain rights in this invention.

FIELD OF INVENTION

This invention relates to killing mosquito larvae, and in particular to applications of using the coating-embedded larvicide to various objects such as tokens, marbles, pebbles, stones, chips, and to peel and stick tapes, which can be adhered to surfaces that can become in contact with water, such as the interior of various water-holding containers, such as flower pots, water-holding dishes used under plant pots, vases, bird baths, fountains, and other similar containers, and the like, and on both manmade and natural surfaces, such as rocks, trees and plants.

BACKGROUND AND PRIOR ART

Over the years, ovitrap type containers have been used and deployed to control mosquitoes. See for example, U.S. Pat. No. 5,983,557 to Perich et al.; U.S. Pat. No. 6,185,861 to Perich; and U.S. Pat. No. 6,389,740 to Perich et al.; and Zeichner, Brian C. "The lethal ovitrap: a response to the resurgence of dengue and chikungunya", U.S. Army Medical Journal, July-September 2011. These types of ovitraps have generally used a wooden stick treated with insecticide that hangs within a cup filled with water up to a series of drain holes. The insecticide strip will hang into the water, with the intention of killing female mosquitoes as they land on the ovitrap to lay eggs. However, these types of Ovitraps have limitations due to the insecticide on the paper breaking down rapidly because of water contact, and also the trap is not designed to kill larvae.

For example, these traps have lacked the use of a timed release of insecticide, and the water ended up breaking down the insecticide to become ineffective or not killing fast enough to prevent egg laying because of insecticide resistance in the mosquito population. A study in Key West, Fla. that used thousands of ovitraps ended up producing mosquitoes from these water filled containers. Additionally, the ovitraps only used an adulticide, which was not effective in killing mosquito larvae.

Still furthermore, Mosquito ovitraps available in the market do not contain larvicide and only adulticide so if eggs are laid larvae can develop. The addition of larvicide would prevent that problem.

Thus, the need exists for solutions to the above problems with the prior art.

SUMMARY OF THE INVENTION

A primary objective of the present invention is to provide dual action lethal containers, apparatus, devices, systems, applications and methods, which are used to kill adult mosquitoes and their larvae.

A secondary objective of the present invention is to provide novel, long-lasting coatings, compositions and formulas that can be used to kill both adult mosquitoes and their larvae.

A third objective of the present invention is to provide mosquito control devices and methods of using and coating water-holding containers, such as but not limited to flower pots, water holding dishes used under plant pots, vases, bird baths, and fountains coated internally with coating containing a mosquito larvicide.

A fourth objective of the present invention is to provide mosquito control devices and methods of coating pebbles, stones, marbles and other types of objects coated with coating-embedded larvicide which can be added to water-holding containers.

A fifth objective of the present invention is to provide mosquito control devices and methods of imbedding objects with durable coatings which releases the larvicide over time so that its action can be prolonged over the duration of a fully season.

A sixth objective of the present invention is to provide for peel and stick mosquito treatments and methods for containers.

A seventh object of the invention is to provide peel and stick tapes, devices, and methods of having insecticide coatings on a top surface of a tape strip and adhesive on a bottom surface of the tape strip for treating water exposed surfaces from mosquitoes.

Long lasting insecticidal coatings used in the invention can prevent quick degradation of insecticidal activity as occurs when insecticides are applied directly to surfaces of lethal ovitraps.

Use of slow release coatings encapsulates most insecticide so that pesticide exposure by humans is minimized when treated surfaces are accidentally contacted.

Use of different active ingredients for elimination of adults and larvae can delay development of pesticide resistance in mosquito populations and provide more efficient control of disease vectors.

Containment of insecticides within an ovitrap can minimize environmental contamination, non-target exposure and chances of accidental insecticide poisoning to humans and animals.

Improvements Over the Prior Art.

The use of long-lasting insecticidal coating provides long-lasting control, as opposed to direct application of insecticides to internal surfaces of lethal ovitraps. The invention has the addition of larvicide to lethal ovitraps. A synergist can be added to the long-lasting coating to overcome insecticide resistance in mosquito populations. The coating not only can protect the insecticidal active ingredient, but also synergists from degradation over time. Additionally, a combination of both an adulticide and a larvicide with a different mode of action in a single coating could allow for easier manufacturing.

Marketing Novelty.

The dual action ovitrap can be sold both in the retail market, for use by homeowners who need to eliminate mosquitoes from their property, and professional market, for use by mosquito control districts, pest control operators, the armed forces, humanitarian institutions and others involved in the control of mosquitoes in different situations.

The long-lasting insecticide coatings can be marketed for other uses where insect control is desired. Such coating could be used in external building walls, internal walls, and any other surfaces where mosquitoes and other pestiferous insects may rest and congregate.

The insecticidal coatings can have colors incorporated that are attractive to mosquitoes. This dual action lethal ovitrap would be useful for control of mosquitoes that vector dengue, west Nile virus, yellow fever, and other pathogens.

Embedding the insecticides in coatings within lethal ovitrap can protect the active ingredient and/or synergist from degradation by the water in the ovitrap, and results in slow release of the active ingredient over time to kill mosquitoes. If the mosquitoes lay eggs before they die, a larvicide also embedded in the coating, is protected from degradation, and slowly releases over time to kill any larvae that hatch from the mosquito eggs. The dual action of the ovitrap assures that the device will not produce mosquitoes as a result of degradation of the active ingredients.

A method of applying mosquito pesticide coated objects into water holding areas, can include the steps of providing a strip treated with a coating with a pesticide, exposing an adhesive surface on the strip, and applying the adhesive surface of the strip against a surface that is exposed to water to treat mosquito larvae.

The providing step can include providing a single polymer coating with an imbedded pesticide and with or without silica to the strip for killing mosquito larvae.

The strip can be selected from paper, plastic, cloth and rubber.

The method can include the step of providing a lower removable protective layer for covering the adhesive surface, wherein removing the lower protective layer allows for the strip to be adhered to the surface that becomes exposed to water.

The method can include the step of providing an upper removable protective layer for covering the insecticide-treated surface, wherein removing the upper protective layer allows for releasing the insecticide.

The method can include the step of leaching out a mosquito killing coating into the water to prevent mosquitoes from breeding in the water.

The surface can be selected from the group consisting of containers, aquariums, flower pots, water holding dishes used under plant pots, vases, bird baths, and fountains and storm water inlets.

The method can include the step of providing a larvicidal coating layer which kills mosquito larvae over time.

The method can include the step of providing an adulticidal coating layer which kills adult mosquitoes over time.

The method can include the step of providing an adulticidal and a larvicidal coating, which kills both adult mosquitoes and their larvae over time.

A peel and stick pesticide coated treatment device to kill mosquitoes, can include a strip treated with a coating having a pesticide, an adhesive surface on the strip; and a lower protective layer covering the adhesive surface, wherein removing the protective layer allows the strip to be applied to a water exposed surface for treating mosquitoes over time.

The strip can be a patch. The strip can include a roll of strips. The roll of strips can include perforations for separating a plurality of strips from one another.

The peel and stick pesticide coated treatment device can include a dispenser for housing the roll of strips. The dispenser can include a cutting edge for allowing a section of the roll to be torn off.

The strip can further include a top protective layer for protecting the coating having the pesticide, the top layer being removed to allow the pesticide to be released.

A peel and stick pesticide coated treatment device, can include a plurality of chips, each chip having an upper surface with a polymer coating imbedded with a pesticide and silica, and an adhesive surface on a lower surface of each chip, wherein the adhesive surface allows for the chip to be adhered to a water exposed surface for treatment against mosquitoes.

Each chip can include a removable upper protective layer for protecting the polymer coating imbedded with the pesticide and silica, and a removable lower protective layer for protecting the adhesive surface.

The removable lower protective layer can include a single elongated strip forming the removable lower protective layer for the plurality of chips.

Further objects and advantages of this invention will be apparent from the following detailed description of the presently preferred embodiments, which are illustrated schematically in the accompanying drawings.

BRIEF DESCRIPTION OF THE FIGURES

FIG. 5A is a right side view of another dual action ovitrap container.

FIG. 5B is a cross-sectional view of the container of FIG. 5A along arrow 5B.

FIG. 6 is a front view of the dual action ovitrap container of FIG. 5 along arrow 6X.

FIG. 7 is a left side view of the dual action ovitrap container of FIG. 5.

FIG. 25A shows a roll of treated peel and stick having mosquitocidal chips (PSMC) with pre-perforations separating sections.

FIG. 28 is an enlarged side cross-sectional view of a single section/patch of a treated peel and stick having mosquitocidal chips (PSMC).

FIG. 29 is an enlarged cross-sectional view of FIG. 28 with the upper and lower protective surface layers removed.

FIG. 30 is an enlarged cross-sectional view of FIG. 29 with the adhesive lower surface attached to a base surface such but not limited to the inner side and/or bottom of a vessel that can hold water.

FIG. 31 shows a flat strip of individual peel and stick chip type discs which can be peeled off and separated from a removable adhesive-protection tape.

FIG. 32 shows an individual peel and stick chip type discs which was separated from a removable adhesive-protection tape.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

A list of the components will now be described.

Figure 1:
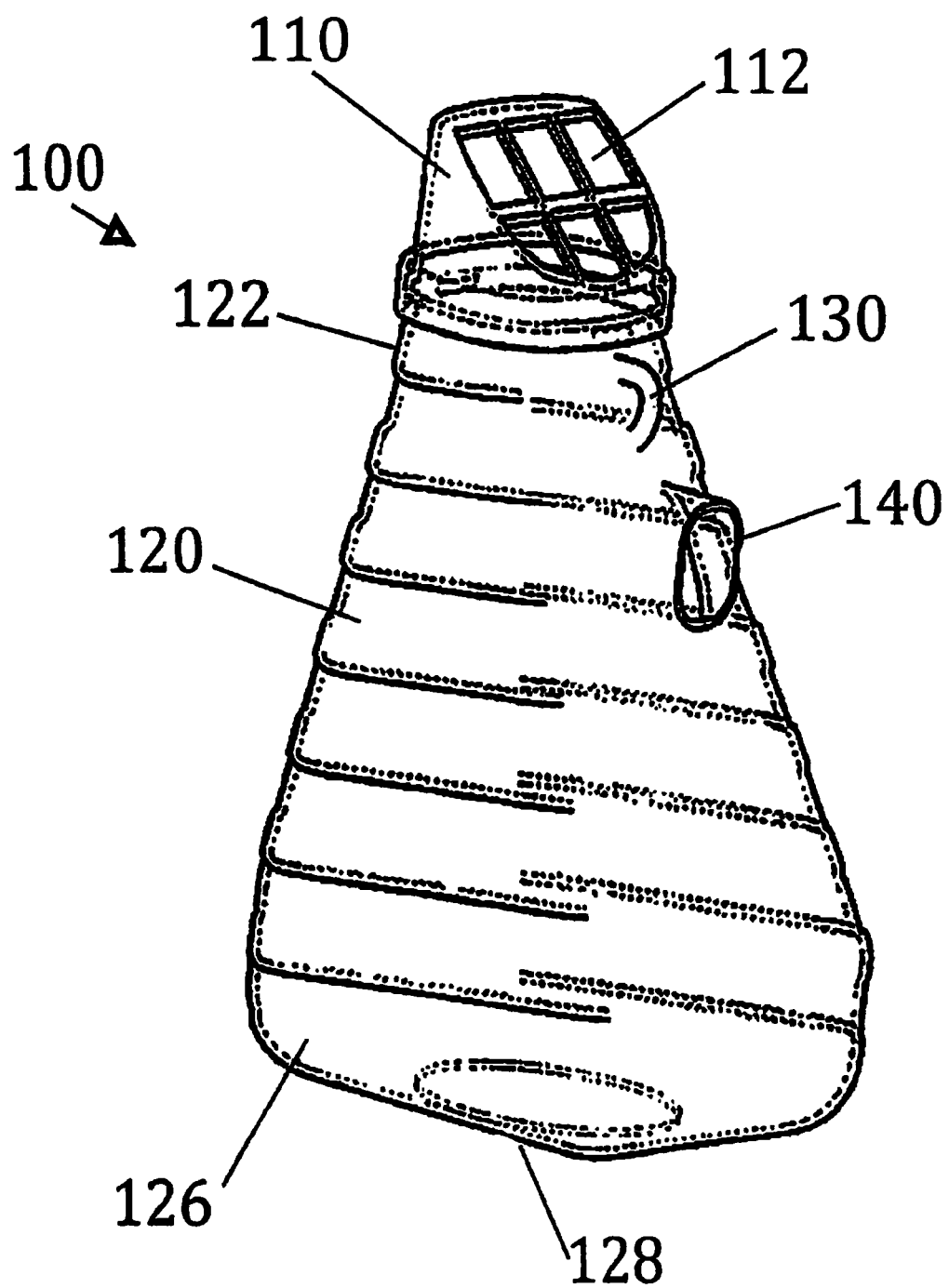
FIG. 1 is a perspective left front side of a first embodiment dual action ovitrap container.
Figure 2:
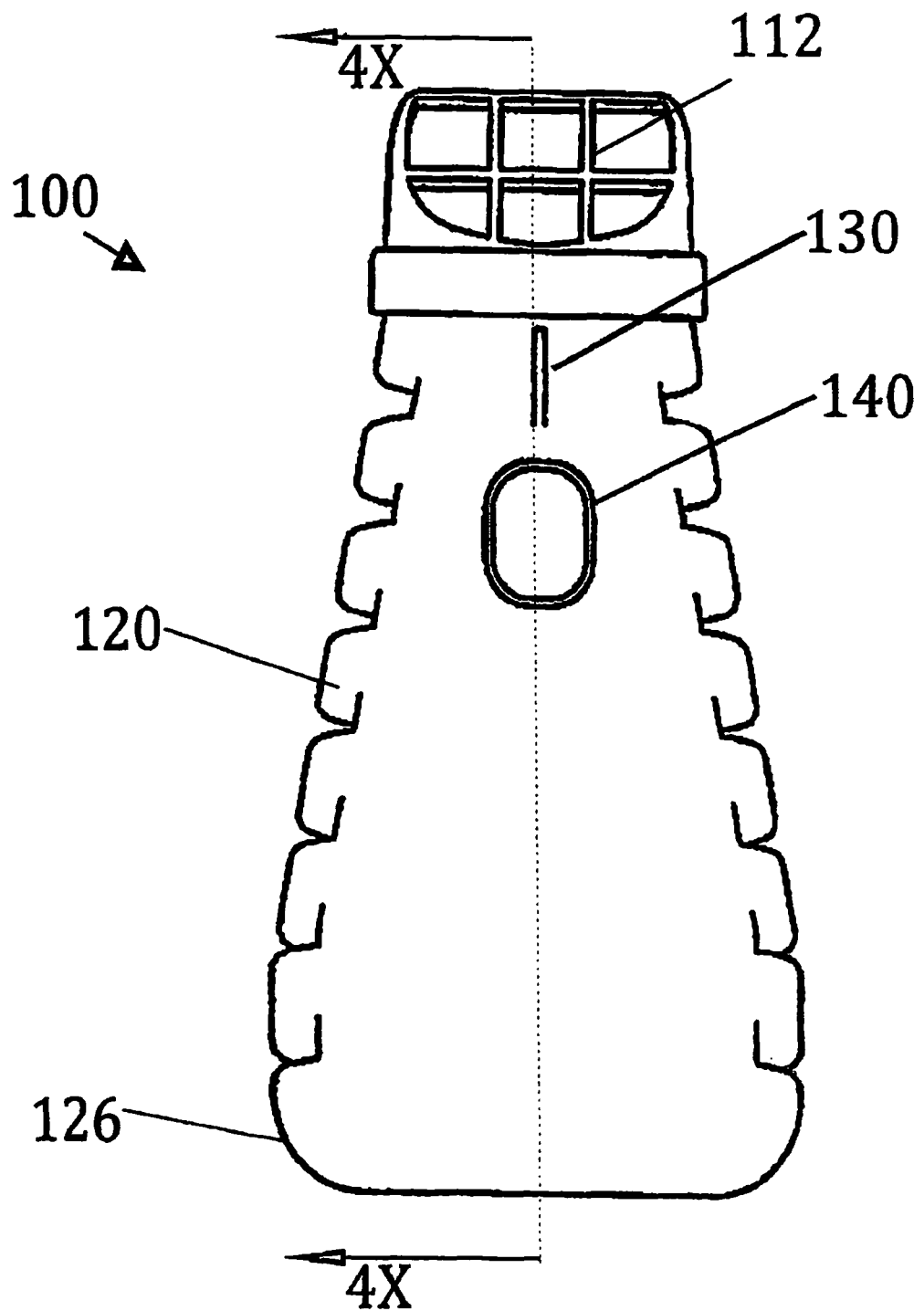
FIG. 2 is a front view of the dual action ovitrap container of FIG. 1.
Figure 3:
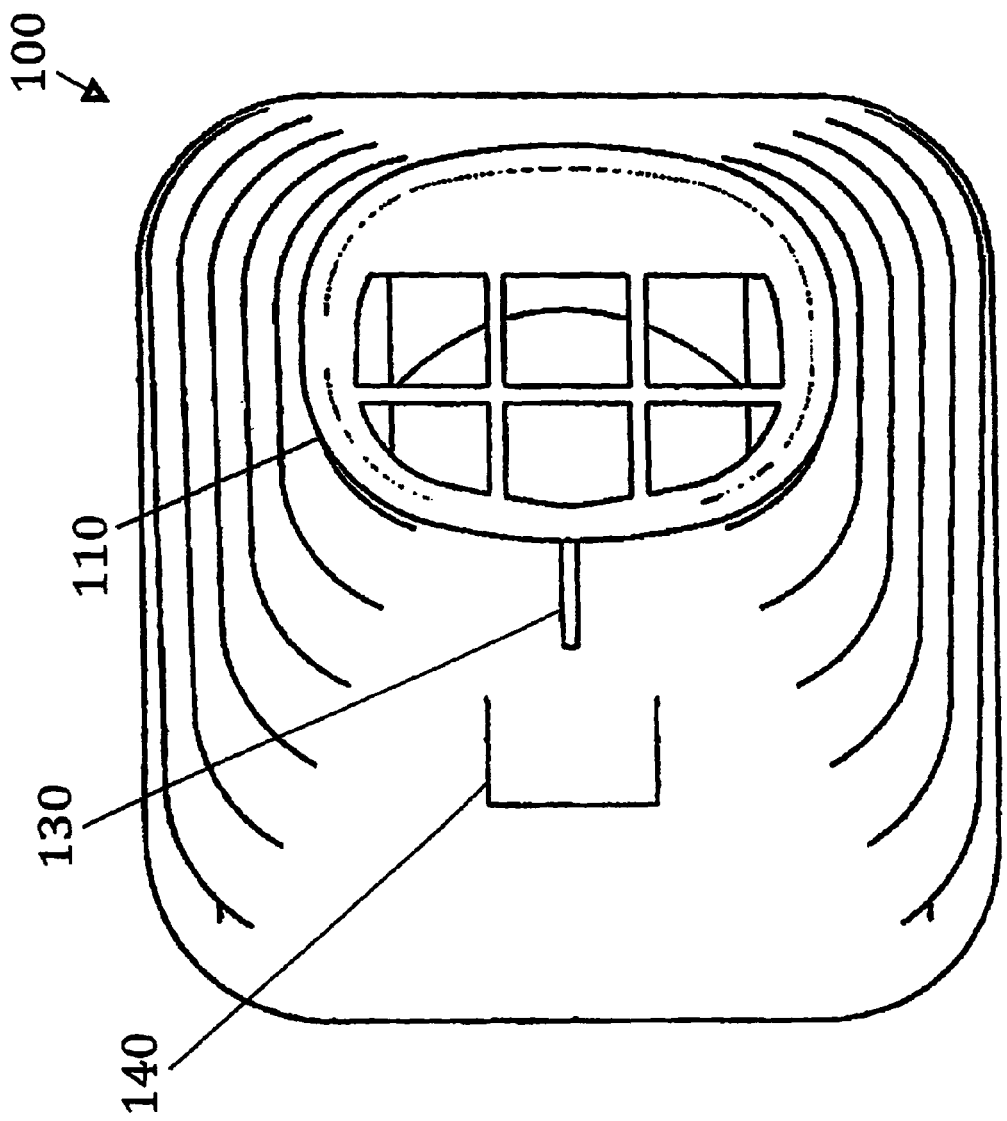
FIG. 3 is a top view of the dual action ovitrap container of FIG. 1.
Figure 4:
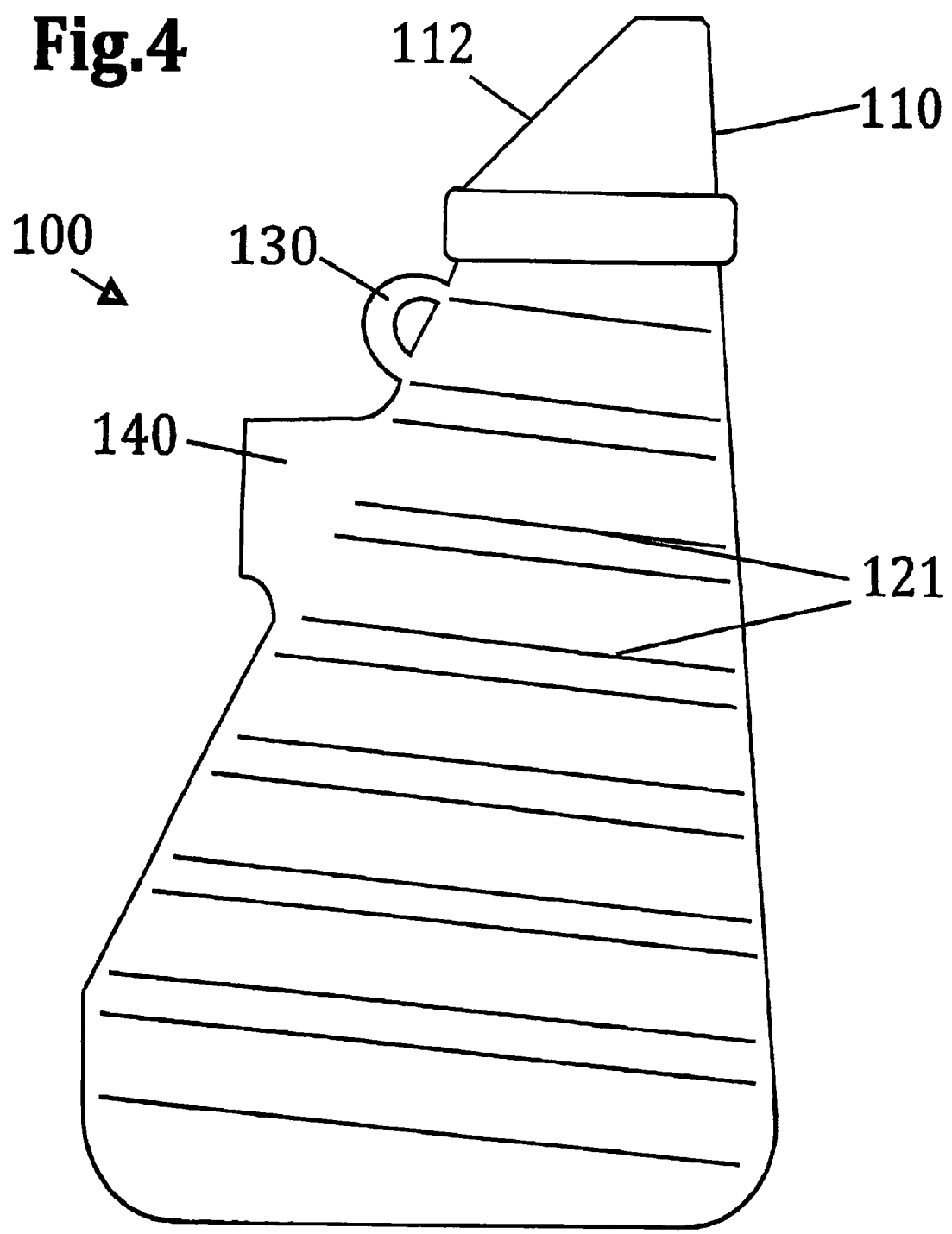
FIG. 4 is a side cross-sectional view of the dual action ovitrap container of FIG. 2 along arrow 4X.

100 First embodiment container
110 narrow cap top on container
112 grate with openings
120 raised ribs
121 internal concave ribs
122 upper end of container
126 lower curved side edges
128 bottom of container
130 hook
140 sideway protruding raised opening
200 First embodiment container
210 narrow cap top on container
212 grate with openings
220 raised ribs
221 inner rib surfaces
222 upper end of container
226 lower curved side edges
228 bottom of container
230 hook
240 sideway protruding raised opening
300 flower pot
310 internal surface of pot
400 plant pot with water dish
420 dish
425 internal surface of dish
430 pot
500 vase
510 internal surface of vase
600 bird bath
610 internal surface of bowl
700 fountain
710 internal surface of fountain
800 coated objects for a storm water inlet
810 interior surface of storm water inlet
900 coated objects for another water holding container
910 interior surface of another container
1000 small mosquito control coated objects
1100 wood stalls and fences and walls and boxes
1200 Roll of treated peel and stick mosquitocidal chip (PSMC) with pre-perforation lines separating sections.
1210 separated section from roll
1211 Removable adhesive protective layer
1212 Chip with lower adhesive surface, and upper surface having coating imbedded with insecticide and silica.
1250 Roll of treated peel and stick mosquitocidal chip (PSMC) without any pre-perforation lines separating sections.
1300 dispenser
1305 cutting edge
1310 Roll of treated peel and stick mosquitocidal chip (PSMC)
1400 vessel for holding water
1450 peel and stick patch section in bottom of vessel.
1500 single section/patch of a treated peel and stick having mosquitocidal chips (objects) (PSMC).
1510 coating layer having an imbedded pesticide
1515 adhesive surface
1520 removal backing layer
1530 peelable outer protective covering layer.
1600 Flat strip of peel and stick chip discs
1610 chip disc 1620 polymer coating layer with imbedded silica and insecticide
1630 adhesive layer
1640 removable adhesive protective tape FIG. 1 is a perspective left front side of a first embodiment dual action ovitrap container 100. FIG. 2 is a front view of the dual action ovitrap container 100 of FIG. 1. FIG. 3 is a top view of the dual action ovitrap container 100 of FIG. 1. FIG. 4 is a side cross-sectional view of the dual action ovitrap container 100 of FIG. 2 along arrow 4X.

Referring to FIGS. 1-4, container 100 can have a modified pyramid shape with rounded sides. Insects such as mosquitoes can enter inside the container through grate 112, and side raised opening 140. The container 100 can include a raised side opening 140 so that water inside the container is maintained to be no higher than the bottom of the side opening 140. Any water inside the container 100 can run out of side opening 140.

On the top of the container 100 can be an attachable cap such as a snap-on cap 110. Alternatively the cap 110 can be threadably attached to the upper portion of the container 100. A grate 112 within openings therethrough can be oriented at an inclined angle and be used to obstruct objects larger than insects, such as but not limited to leaves, branches, hands, fingers and the like, from entering container 100.

The narrow opening can create dead-air, high humidity conditions that mosquitoes prefer as oviposition and resting sites. A narrow opening can also prevent excessive rain from entering and rinsing larvicide from the interior of the ovitrap. The narrow opening also can prevent dilution of the larvicide and adulticide active ingredients which can slowly escape from the coatings in order to control mosquitoes.

The inclined grate 112 opening increases the attractiveness of the trap for the mosquito. A horizontal oriented grate would not be as effective an attractant opening as an inclined grate. The inclined grate 112 also more closely replicates an opening in a tree which is usually not horizontal and the tree opening which can hold water is the most attractive hatching condition for attracting mosquitoes into the container 100.

A built on hook 130, such as a loop, can be used to hang the container 100 in an elevated position such as but not limited to hanging the container 100 from a branch, under a tree, and the like. The novel ovitrap 100 can be deployed on a surface through bottom 128 or hanging by hook 130 from a support, as opposed to single-action ovitraps that need to be placed on a completely horizontal surface. The hook 130 offers many more opportunities for placement of ovitraps in locations that are more attractive to mosquitoes and protected from animal activities, as well as in conditions that prevent disturbances by children.

Raised ribs 120 on the container 100 form concave curved stacked sections 121 inside the container 100. The stacked concave interior surfaces 121 allow for an easier landing surface for the mosquitoes to land on and hatch. The ribs 120 and interior surfaces 121 are slightly inclined so that when water evaporates and goes down, each rib section 120 and corresponding interior surface 121 have a section above and below the water level.

The ribs 120 and interior surfaces 121 have the effect of limiting the wind turbulence that can enter inside of the container 100 through the side opening 140 and grate 112. Incoming wind can cause a Venturi effect inside the container 100. The inside stacked concave rib sections 121 can reduce the Venturi effect and any turbulence inside the container 100. This is very important since Mosquitoes prefer to lay eggs when there is less or no wind.

The bottom 128 of the container 100 can be flat to allow for the container stability to stand on its' own on a ground or raised flat surface, with lower side curved edges 126.

The inside walls of the container can be coated with a single coating having both larvicide and adulticide described in reference to the tables below. The double coating can be coated on interior walls and the floor both below and above the water line formed from side opening 140.

The container 100 can be formed from molded plastic material such as those used to form water bottles and the like, with a rougher interior surface.

The plastic container 100 can be pretreated in order to make the interior surface coatings rough and not too smooth, in order to provide cavities of approximately 150 to approximately 500 µm wide.

Mosquitoes prefer to deposit eggs in indentations on the surface of containers. Laboratory testing for desired cavity sizes was done at the University of Florida, Gainesville, Fla. in the summer of 2013, where the inventors modified wood surfaces (using popsicle sticks), and glued plastic mesh on top of the sticks. Six different sizes of mesh were tested, each being placed in a cup of water, which were placed in a lab cage where mosquitoes were present. The holes of the mesh became the sides of the cavities and the wood being the bottom of the cavities. The materials were left untreated, and testing and observations was completed to determine which mesh size was most desirable for the female mosquitoes to lay their eggs. Laboratory testing determined the highest results of killed mosquitoes occurred with mesh cavity having dimensions of approximately 250 µm wide. A range of approximately 150 to approximately 500 µm wide was also determined to cover desirable mesh size cavities. The term approximately can include +/−10%. The textured internal surfaces with formed cavities demonstrate that optimum resting and oviposition can be obtained by modifying the coatings accordingly.

The interior walls surfaces of the containers 100 can be roughened into having textured surfaces with cavities by at least three different processes.

One process can include using a plastic or material that inherently has a rough surface. The plastic can be formed from molds that form selected cavity sizes on the interior surfaces of the plastic container.

Another process can include re-treating the interior surfaces of a container, such as plastic with a separate textured material coating that artificially forms a roughened surface. For example, a paintable primer, or a sprayable primer, and the like, can be used. The textured material coatings can be selected in order to create the selected cavity sizes based on applying those material coatings to the surfaces of the container.

Mosquitoes can enter either by the top or the side entry into the container (which can have a partial bottle configuration. The mosquitoes have a choice of vertical and horizontal surfaces to rest, all of which are coated with insecticidal coating. Any coating and/or primer can be applied inside the container by various techniques such as but not limited to inserting a spray nozzle in the bottle and spraying aground to cover 360° internally below a selected level.

A still another process can include adding additional grains such as but not limited to sand, acrylics, into the insecticide coating, which can then be coated to the interior surfaces of the container which forms a roughened surface, having the selected cavity sizes. Similarly, techniques to spray inside the container can include but are not limited to having any coating and/or primer can be applied by inserting a spray nozzle into the opening(s) of the container and spraying around to cover 360° internally below a selected level.

The outside of the container 100 can have different colors. The exterior of container can be darkened to black, brown, and other dark colors that replicate a tree type structure. For example, a dark color attracts mosquitoes.

The cap 110 can have a different color such as red that causes contrast with the dark color of the rest of the container 100, which would replicate surfaces of the tree having wet and dry areas. Mosquitoes associate red and black to ideal tree surface locations.

The side opening 140 and the grate opening also appear to replicate a tree surface along with the coloring of the container surface, which are attractive to mosquitoes.

The inside of the container 100 can include a separate mosquito attractant either or both embedded into the coating or loose inside the container 100. The attractant can include but it not limited to broken leaves, artificial and natural scents, contained or not in cloth, paper, or mesh bag similar to a teabag that can replicate moist wet areas that are normally attracted to mosquitoes.

The object of the interior surface of the container with or without the attractant is to form an attractant environment and not a repellant environment for mosquitoes.

Table 1 lists examples of adulticide and larvicidal coating ingredients that can be used in the interior coatings of the container 100 along with a range for each components and preferred percentage for combined adultacidal and larvacidal coating.

TABLE 1

| Main Ingredients | Choice Ingredients | Preferred Range | Preferred Exemplary Amount |
|---|---|---|---|
| Choice of Coating | | 83.0-99.9989% | 98.59% |
| Acrylic paint | | | |
| Oil based paint | | | |
| Plastic polymer | | | |
| Choice of Adulticidal Active Ingredient: | | 0.001-5.0% | 0.7% |
| Pyrethroid insecticide | | | |
| Organophosphate insecticide | | | |
| Carbamate insecticide | | | |
| | Permethrin (pyrethroid) | 0.2-5.0% | 0.7% |
| | Cypermethrin (pyrethroid) | 0.02-5.0% | 0.1% |
| | Deltamethrin (pyrethroid) | 0.001-5% | 0.06% |
| | Bifenthrin (pyrethroid) | 0.001-5% | 0.06% |
| | Chlorpyrifos (organophosphate) | 0.2-5.0% | 0.5% |
| | Propoxur (carbamate) | 0.2-5.0% | 0.5% |
| | Diazinon (organophosphate) | 0.2-5.0% | 1.0% |
| Choice of Larvicidal Active Ingredient: | | 0.0001-2% | 0.01% |
| | Bacillus thuringiensis israelensis | 0.0001-2% | 0.01% |
| | Methoprene | 0.0001-2% | 0.01% |
| | Pyroproxifen | 0.0001-2% | 0.01% |
| | Spinosad | 0.0001-2% | 0.01% |
| Choice of Synergist: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

Table 2 lists the main components along with a range for each components and preferred percentage for an adultacidal coating.

TABLE 2

| Main Ingredients | Choice Ingredients | Preferred Range | Preferred Exemplary Amount |
|---|---|---|---|
| Choice of Coating | | 85.0-98.999% | 98.6% |
| Acrylic paint | | | |
| Oil based paint | | | |
| Plastic polymer | | | |
| Choice of Adulticidal Active Ingredient: | | 0.001-5.0% | 0.7% |
| Pyrethroid insecticide | | | |
| Organophosphate insecticide | | | |
| Carbamate insecticide | | | |
| | Permethrin (pyrethroid) | 0.2-5.0% | 0.7% |
| | Cypermethrin (pyrethroid) | 0.02-5.0% | 0.1% |
| | Deltamethrin (pyrethroid) | 0.001-5% | 0.06% |
| | Bifenthrin (pyrethroid) | 0.001-5% | 0.06% |
| | Chlorpyrifos (organophosphate) | 0.2-5.0% | 0.5% |
| | Propoxur (carbamate) | 0.2-5.0% | 0.5% |
| | Diazinon (organophosphate) | 0.2-5.0% | 1.0% |
| Choice of Synergist: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

Table 3 lists the main components along with a range for each components and preferred percentage for larvacidal coating.

TABLE 3

| Main Ingredients | Choice Ingredients | Preferred Range | Preferred Exemplary Amount |
|---|---|---|---|
| Coating (choice of one) | | 88.0-99.9999% | 99.82% |
| Acrylic paint | | | |
| Oil based paint | | | |
| Plastic polymer | | | |
| Choice of Larvicidal Active Ingredients: | | 0.0001-2% | 0.01% |
| | Bacillus thuringiensis israelensis | 0.0001-2% | 0.01% |
| | Methoprene | 0.0001-2% | 0.01% |
| | Pyroproxifen | 0.0001-2% | 0.01% |
| | Spinosad | 0.0001-2% | 0.01% |
| Choice of 1-3 Synergists: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

The interior surface coatings can include those described and used in related U.S. patent application Ser. No. 13/866,656 to Koehler et al. which is assigned to the same assignee as that of the subject invention, and which is incorporated by reference in its' entirety.

Figure 8:
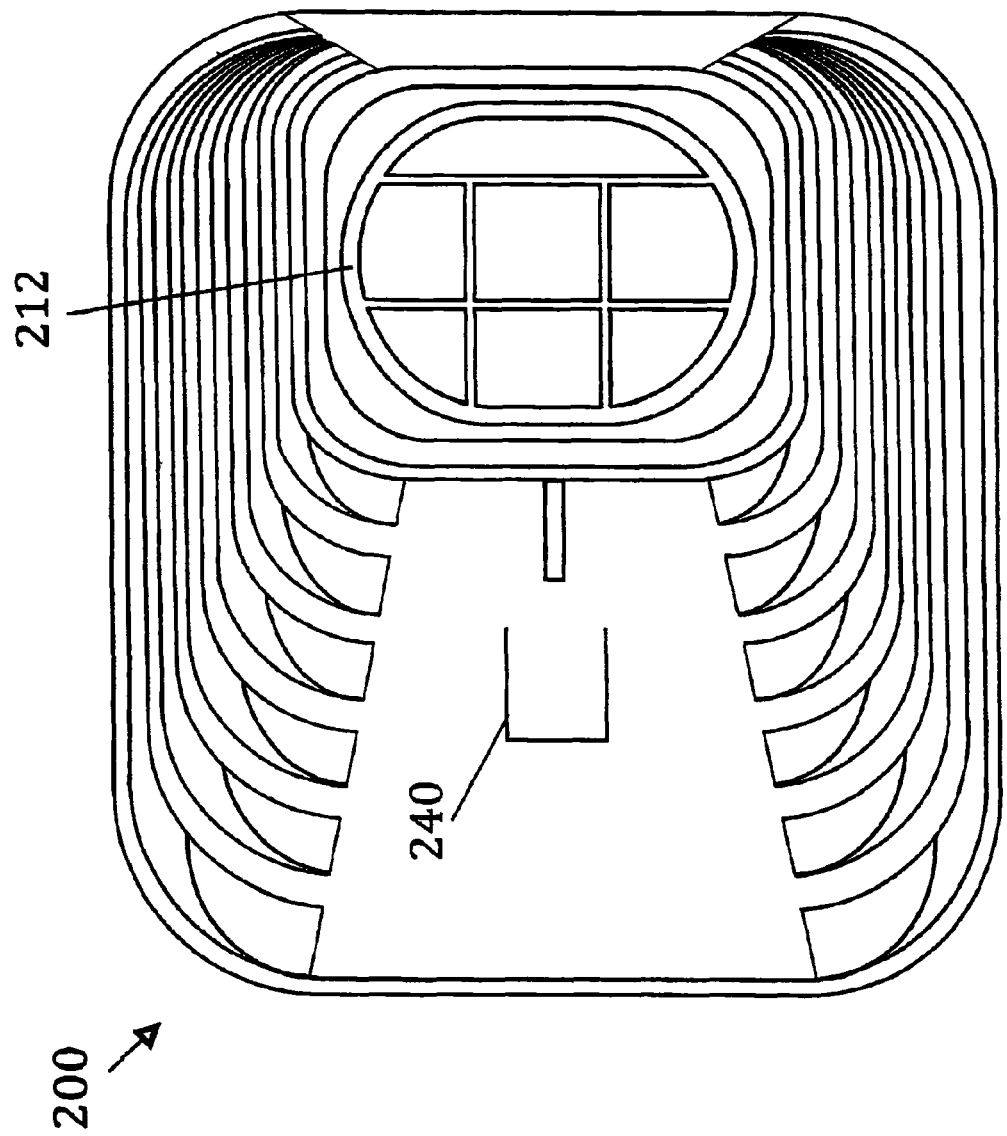
FIG. 8 is a top view of the dual action ovitrap container of FIG. 5 along arrow 8X.

FIG. 5A is a right side view of another dual action ovitrap container 200. FIG. 5B is a cross-sectional view of the container of FIG. 5A along arrow 5B. FIG. 6 is a front view of the dual action ovitrap container 200 of FIG. 5 along arrow 6X. FIG. 7 is a left side view of the dual action ovitrap container 200 of FIG. 5. FIG. 8 is a top view of the dual action ovitrap container 200 of FIG. 5 along arrow 8X.

Referring to FIGS. 5A-8, part numbers 210, 212, 220, 221, 222, 226, 228, 230, 240 correspond and function to similar part numbers 110, 112, 120, 121, 122, 126, 128, 130 and 140 in the previous embodiment. In these figures, the bottom of the container 200 can have a length between the back and front of approximately 5 inches and a width between the left side and right side of approximately 4¾ inches, and a height between the bottom 228 and the upper end of the container 200 being approximately 4½ inches from the bottom 228 of the container 200, with the upper end having a length of approximately 2⅛ inches and a width of approximately 2¾ inches. The parallel raised ribs 220 can be spaced apart from each other by approximately ½ inch and each rib can be approximately ½ inch thick, and can extend outward from the sides of the container 200 by approximately ⅜ of an inch. Each of the ribs 220 can be angled downward from the front of the container to the rear of the container. At the bottom 228 of the container 200, the lowest rib can start approximately 1¼ inches from the front of the container 200 and angle downward to be approximately 1 inch from the rear of the container 200.

The ribs 220 and interior surfaces 221 have the effect of limiting the wind turbulence that can enter inside of the container 200 through the side opening 240 and grate 212. Incoming wind can cause a Venturi effect inside the container 200. The inside stacked concave rib sections 221 can reduce the Venturi effect and any turbulence inside the container 200. This is very important since Mosquitoes prefer to lay eggs when there is less or no wind.

The novel ovitrap internal incline plane rib surfaces offer both horizontal and vertical surfaces for female mosquitoes to oviposit and rest. This configuration makes these surfaces available to oviposition and resting regardless of the level of the water in the ovitrap. All of these surfaces can be coated with the coating-embedded larvicides and adulticides.

The inclined grate 212 can have a generally oval shape with a width of approximately 2¾ inches. The sideway protruding opening 240 can be generally oval shape with a height of approximately 1⅛ inches and a width of approximately ⅞ inch. Other dimensions are shown in the figures.

The coatings described above, and all their applications with the containers 100, 200 can be used with other water holding containers, and objects.

Figure 9:
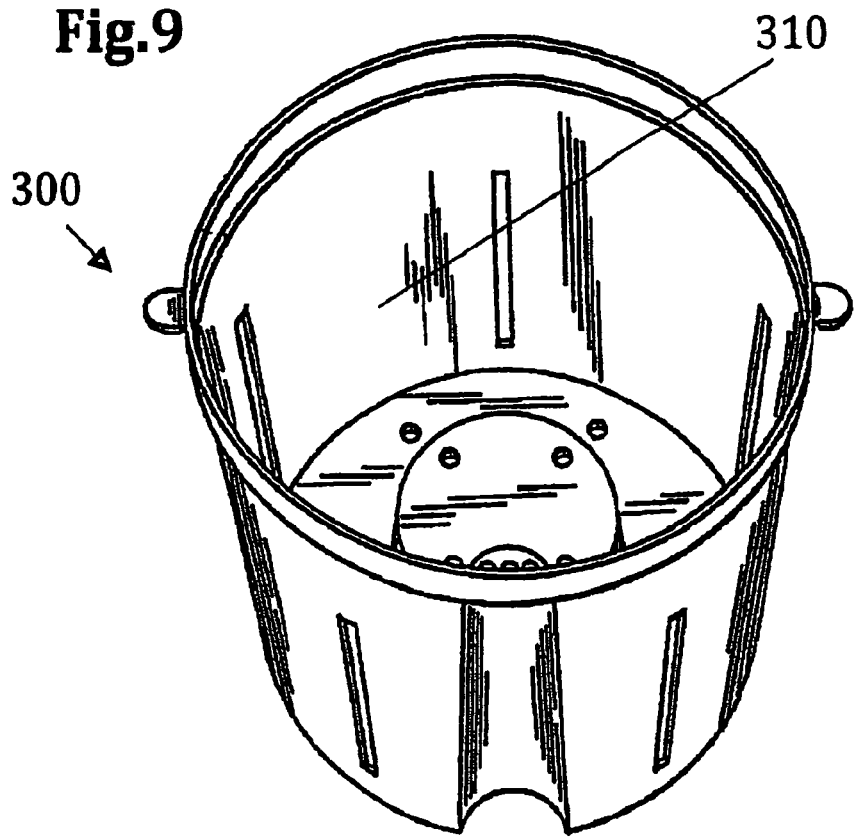
FIG. 9 shows another embodiment of using the novel coatings with a flower pot.

FIG. 9 shows another embodiment of using the novel coatings with a flower pot 300. The internal surface 310 can be coated with coatings containing a mosquito larvicide coatings.

Figure 10:
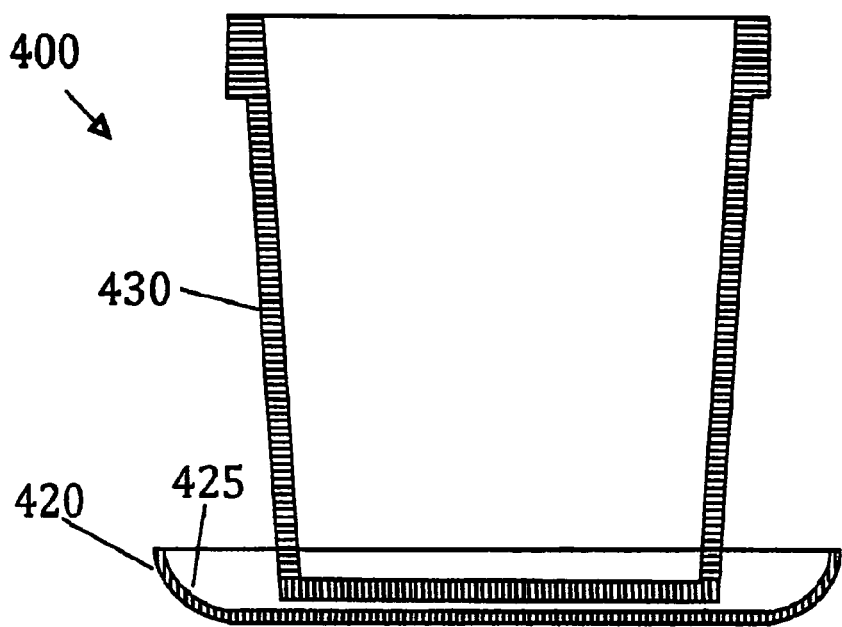
FIG. 10 shows another embodiment of using the novel coatings with water-holding dishes used under a plant pot.

FIG. 10 shows another embodiment of using the novel coatings with a water holding dishes 420 used under a plant pot 430. The internal surface 425 of the dish 420 can be coated with coatings containing a mosquito larvicide coatings.

Figure 11:
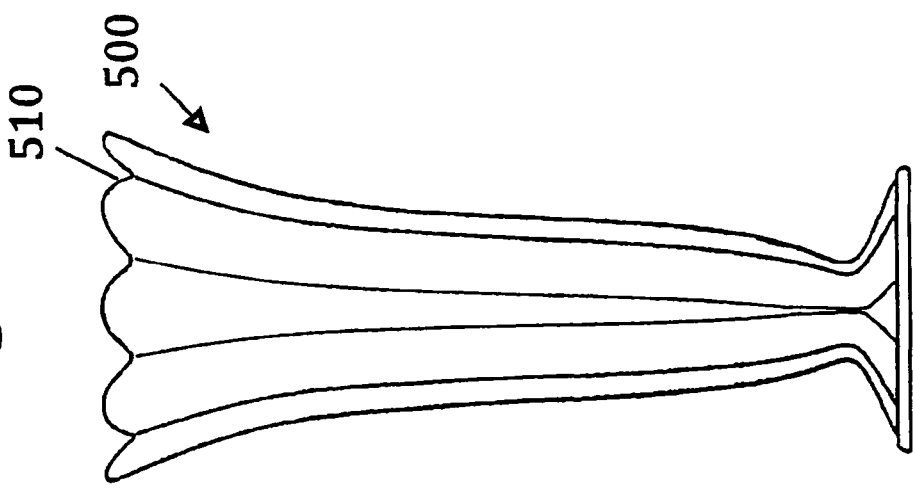
FIG. 11 shows another embodiment of using the novel coatings with a water-holding vase.

FIG. 11 shows another embodiment of using the novel coatings with a water holding vase 500. The internal surface 510 of the vase 500 can be coated with coatings containing a mosquito larvicide coatings.

Figure 12:
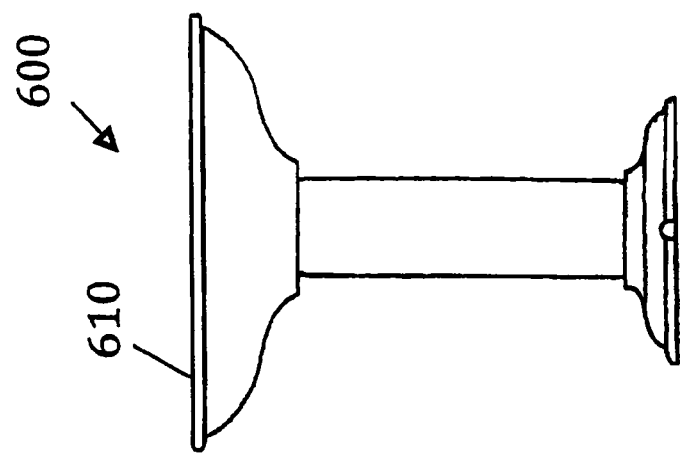
FIG. 12 shows another embodiment of using the novel coatings with a water-holding bird bath.

FIG. 12 shows another embodiment of using the novel coatings with a water holding bird bath 600. The internal surface 610 of the bath bowl can be coated with coatings containing a mosquito larvicide coatings.

Figure 13:
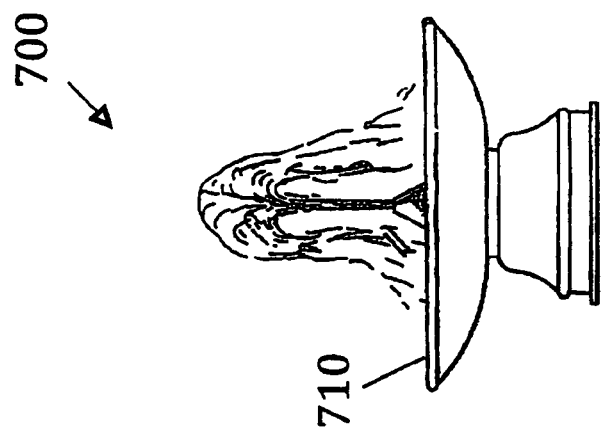
FIG. 13 shows another embodiment of using the novel coatings with a water-holding fountain.

FIG. 13 shows another embodiment of using the novel coatings with a water holding fountain 700. The internal surface 710 of the fountain can be coated with coatings containing a mosquito larvicide coatings.

Additional mosquito control objects 1000 can be coated with larvicide such as but not limited to pebbles, stones, marbles and other types of objects coated with coating-embedded larvicide. These small coated objects can be placed in water holding containers such as but not limited to using untreated containers previously described or other types of containers so that the larvicide can leach out over time.

Additionally, the interior coated water holding containers can also have the small coated objects 100 dropped inside the containers.

Figure 14:
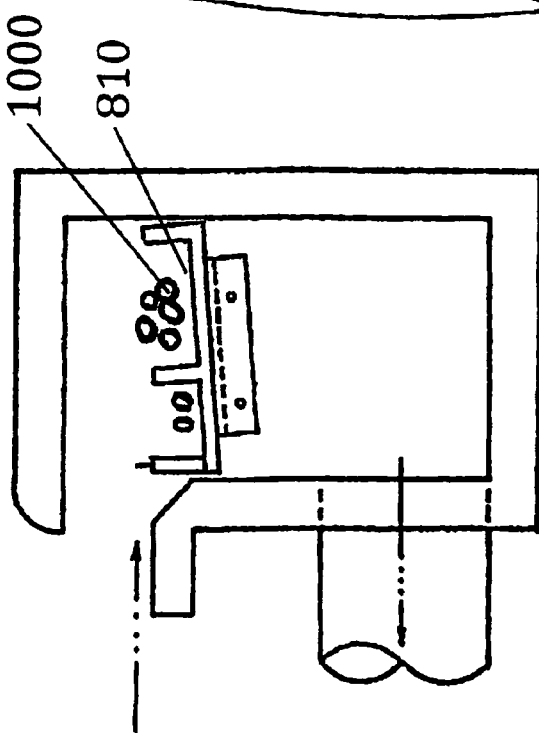
FIG. 14 shows another embodiment of using the novel coatings with small objects in a water-holding storm-water inlet.

FIG. 14 shows another embodiment of using the novel coatings with a small coated objects 1000 in a water holding storm water inlet 800. Alternatively internal surface areas 810 in the storm water inlet can also be coated with coatings containing mosquito larvicide coatings. The small coated objects can also be dropped into standing water in storm water inlets and the like so as to prevent those areas from becoming larvae breeding grounds. Also any other type of standing water can use the coated small objects dropped into the standing water.

Figure 15:
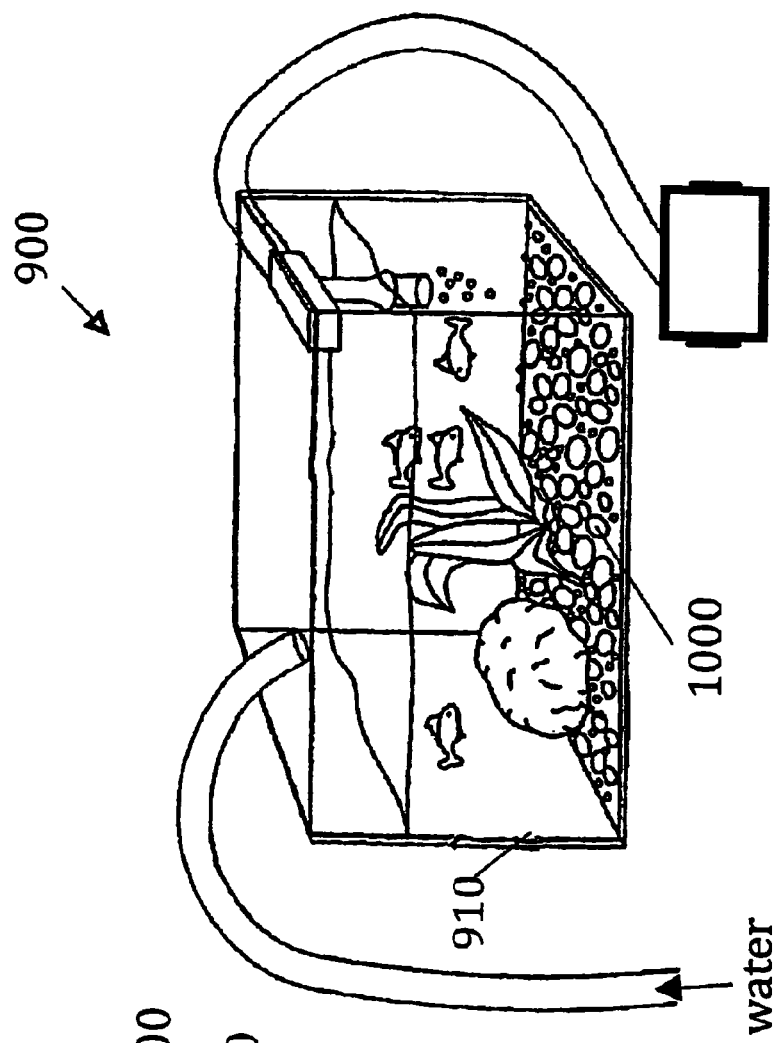
FIG. 15 shows another embodiment of using the novel coatings with small objects that can be used with another water-holding area.

FIG. 15 shows another embodiment of using the novel coatings with a small coated objects 1000 in another water holding container 900 such as an aquarium. Alternatively, internal surface areas 910 can also be coated with coatings containing mosquito larvicide coatings.

Figure 16:
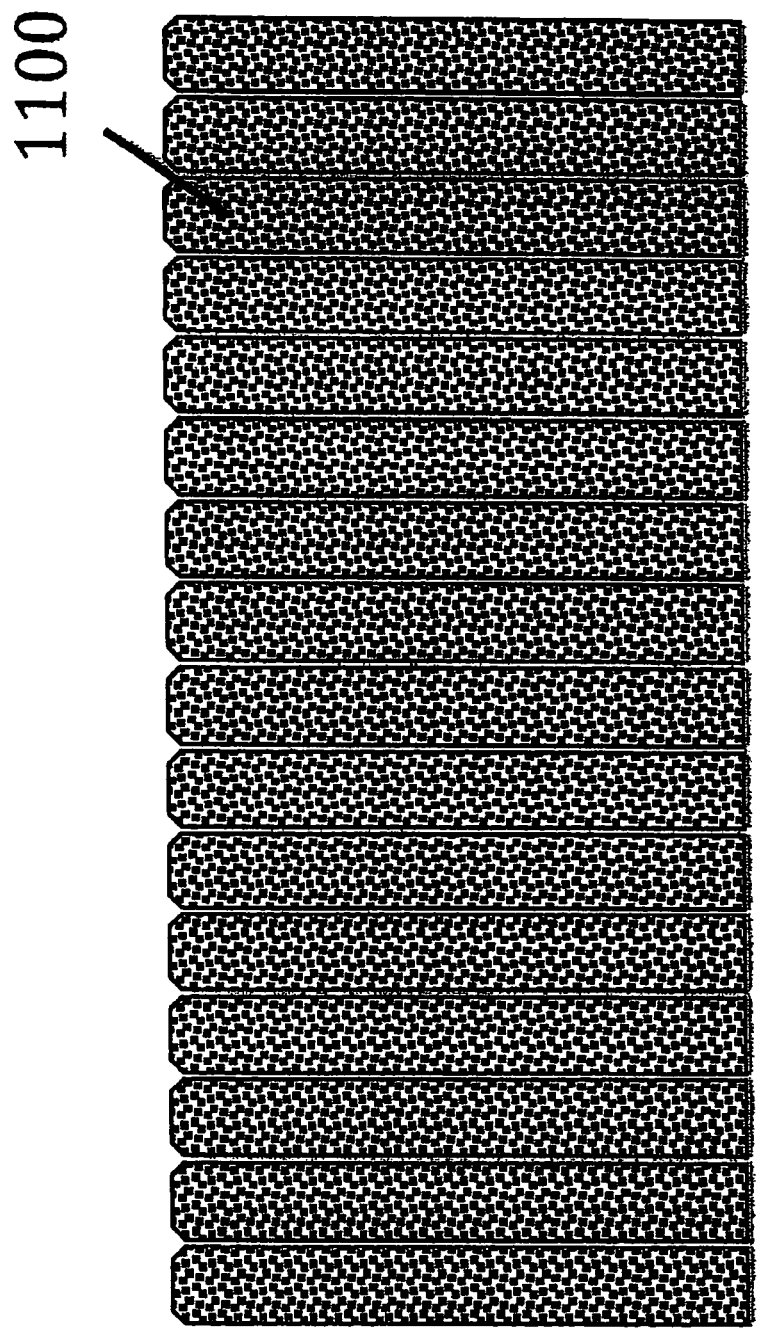
FIG. 16 shows another embodiment of using the novel coatings on wood surfaces, such as stalls and fences and walls.

FIG. 16 shows another embodiment of using the novel coatings on wood surfaces 1100, such as wooden stalls for horses and fences and walls and boxes, and the like. Other surfaces that can become damp and wet, such as but not limited to other wood surfaces and the like, can also be treated with the coatings.

FIGS. 17-24 show the results of testing using the containers and different coatings of the first two embodiments of the invention described above for killing mosquitoes.

Figure 17:
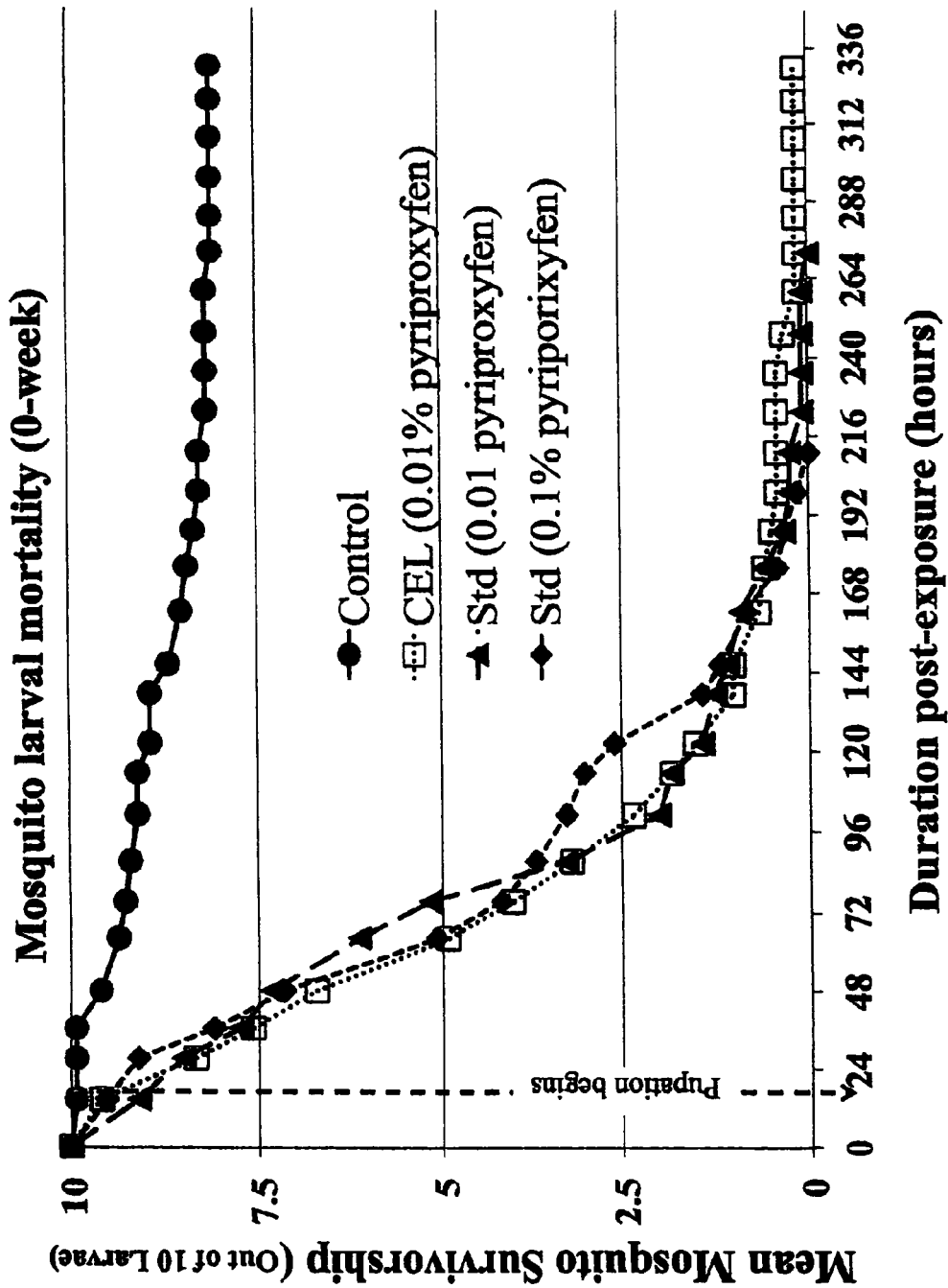
FIG. 17 is a graph of mosquito larval mortality after 0-week aging with the average live mosquitoes on the vertical axis versus exposure time on the horizontal axis.

FIG. 17 is a graph of mosquito larval mortality over 0-week aging with amount of mosquitoes on the vertical axis versus exposure time on the horizontal axis.

Figure 18:
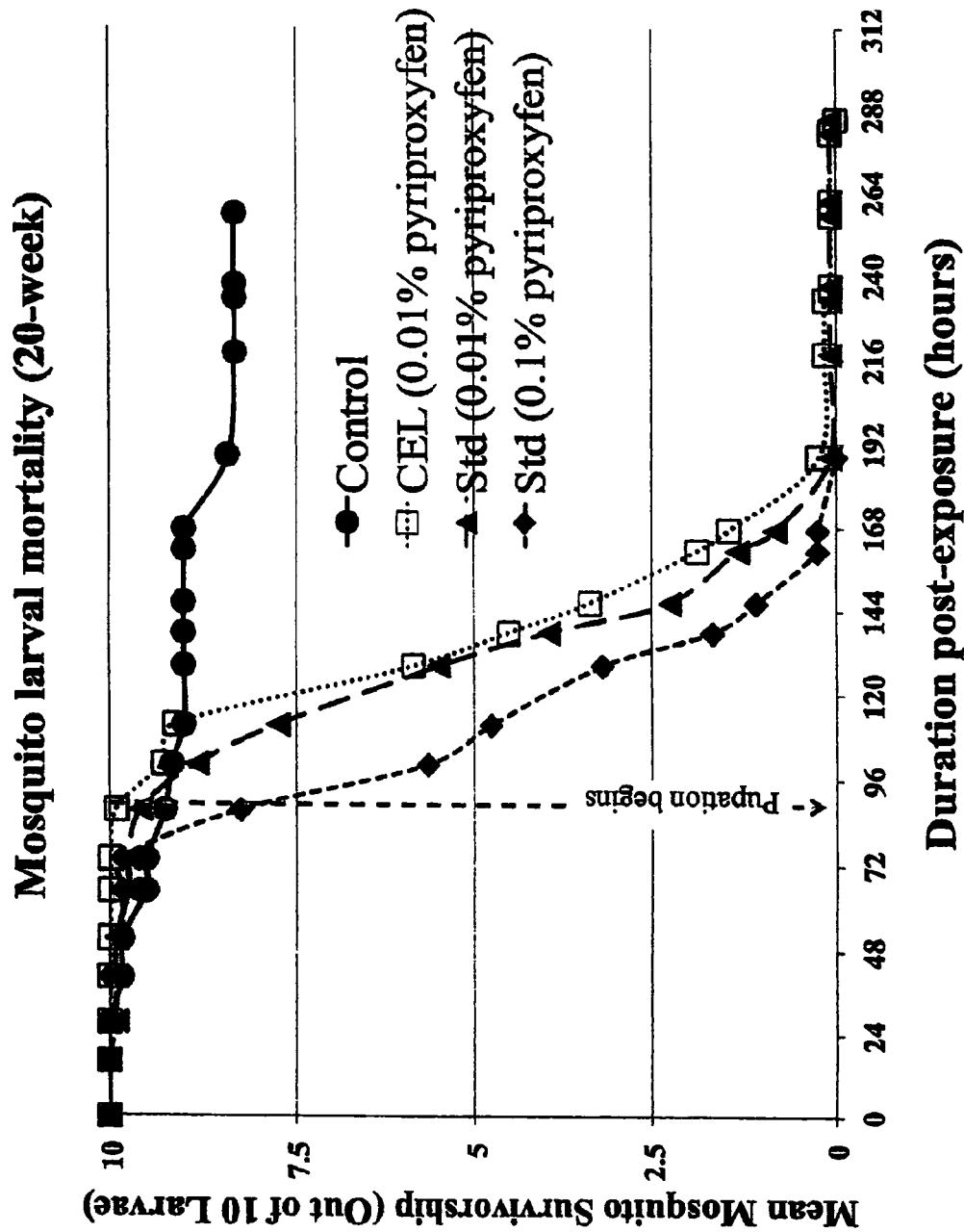
FIG. 18 is a graph of mosquito larval mortality after 20-week aging with the average live mosquitoes on the vertical axis versus exposure time on the horizontal axis.

FIG. 18 is a graph of mosquito larval mortality over 20-week aging on the vertical axis versus exposure time on the horizontal axis.

Figure 19:
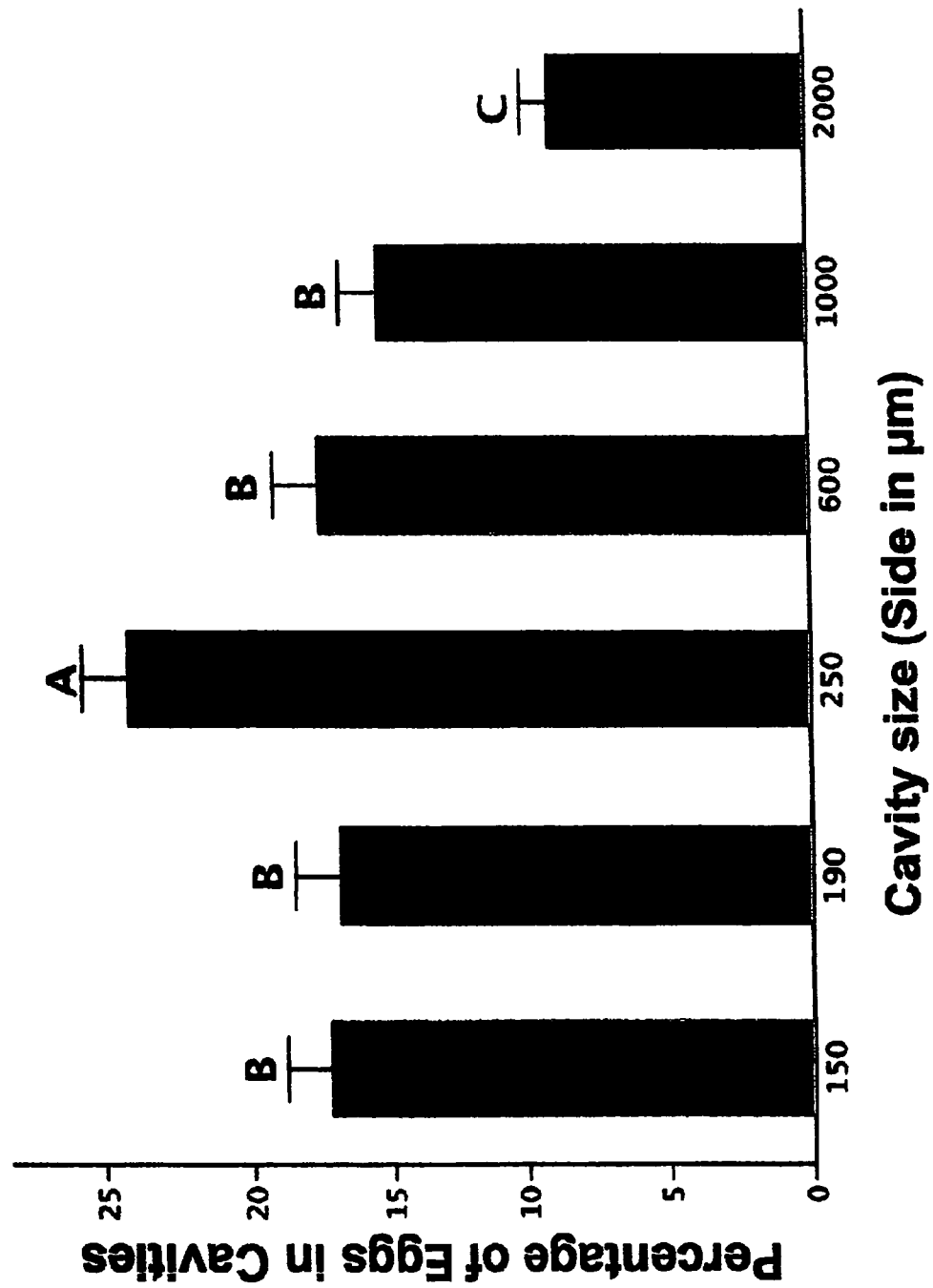
FIG. 19 is a graph of percent of mosquito eggs on the vertical axis versus cavity size on the horizontal axis.

FIG. 19 is a graph of percent of mosquito eggs on the vertical axis versus cavity size on the horizontal axis.

Figure 20:
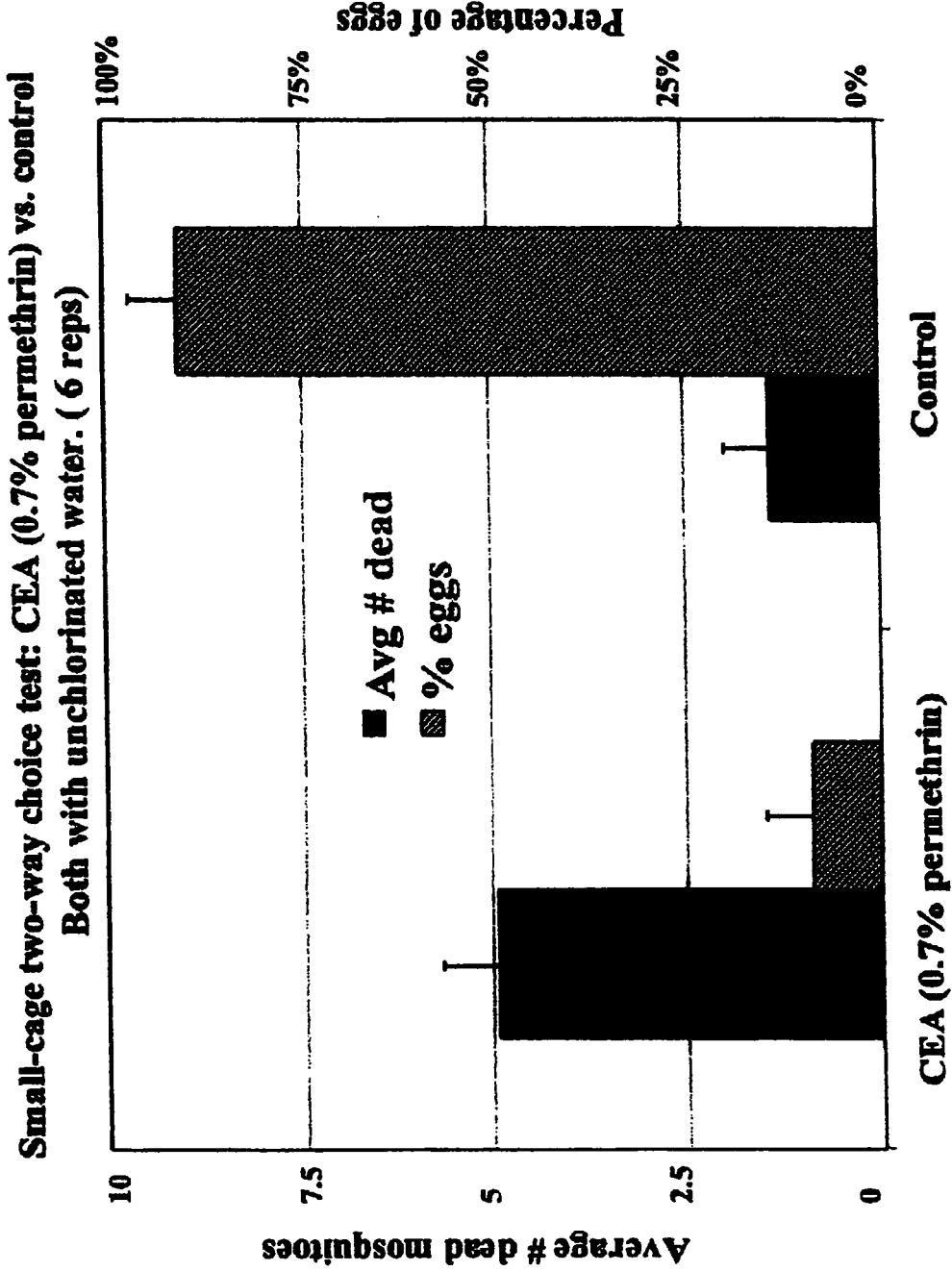
FIG. 20 shows a bar graph of results of a two-way choice test for mosquito females placed in a small-cage with containers with CEA (0.7% permethrin) vs. control, both using unchlorinated water, with number of dead mosquitoes and percentage of eggs found in each treatment on the vertical axis.

FIG. 20 shows a bar graph of results of a two-way choice test for mosquito females placed in a small-cage with containers with CEA (0.7% permethrin) vs. control, both using unchlorinated water, with number of dead mosquitoes and percentage of eggs found in each treatment on the vertical axis.

Figure 21:
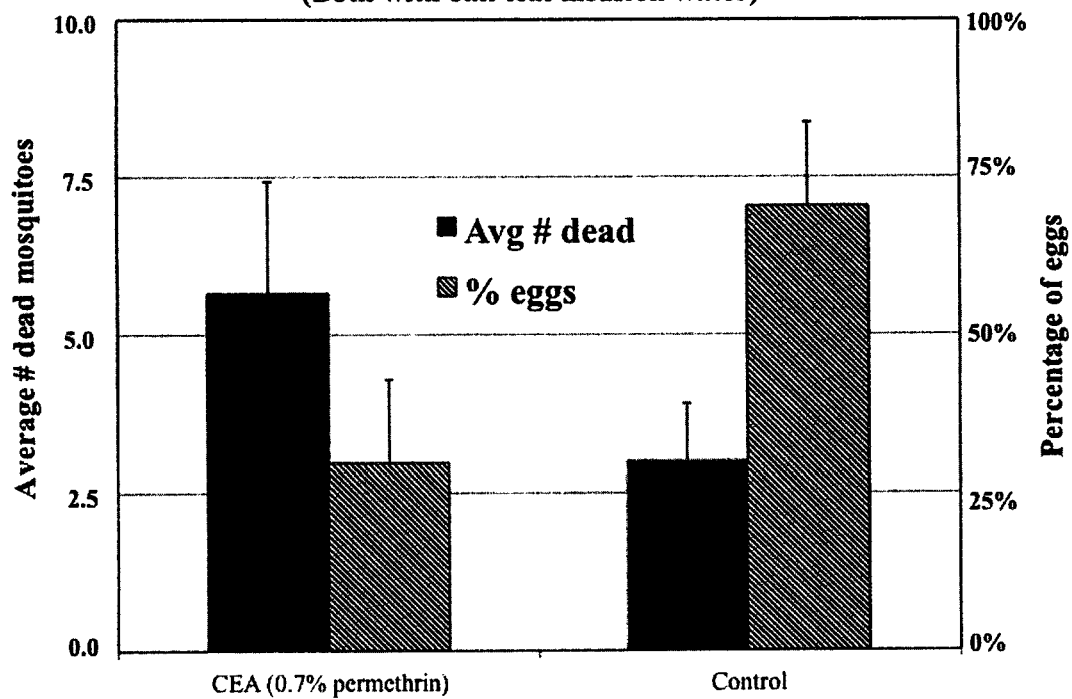
FIG. 21 shows a bar graph of results of a two-way choice test for mosquito females placed in a small-cage with containers with CEA (0.7% permethrin) vs. control, both with oak-leaf infusion water, with number of dead mosquitoes and percentage of eggs found in each treatment on the vertical axis.

FIG. 21 shows a bar graph of results of a two-way choice test for mosquito females placed in a small-cage with containers with CEA (0.7% permethrin) vs. control, both with oak-leaf infusion water, with number of dead mosquitoes and percentage of eggs found in each treatment on the vertical axis.

Figure 22:
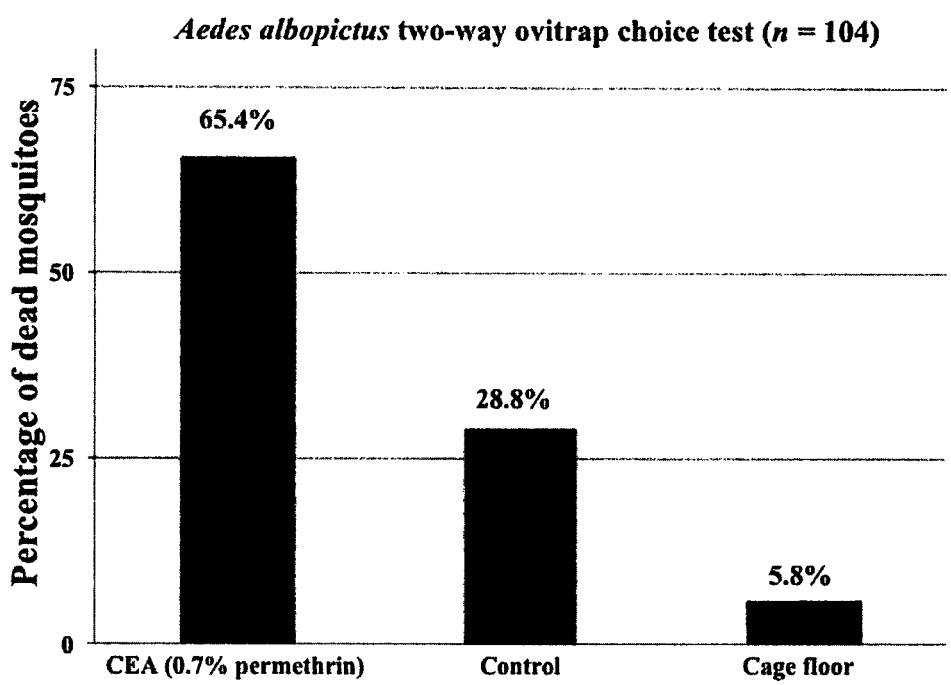
FIG. 22 shows a bar graph of a two-way ovitrap choice test with *Aedes albopictus*, with percentage of mosquitoes on the vertical axis versus the location where they were found.

FIG. 22 shows a bar graph of a two-way ovitrap choice test with *Aedes albopictus*, with percentage of mosquitoes on the vertical axis versus the location where they were found.

Figure 23:
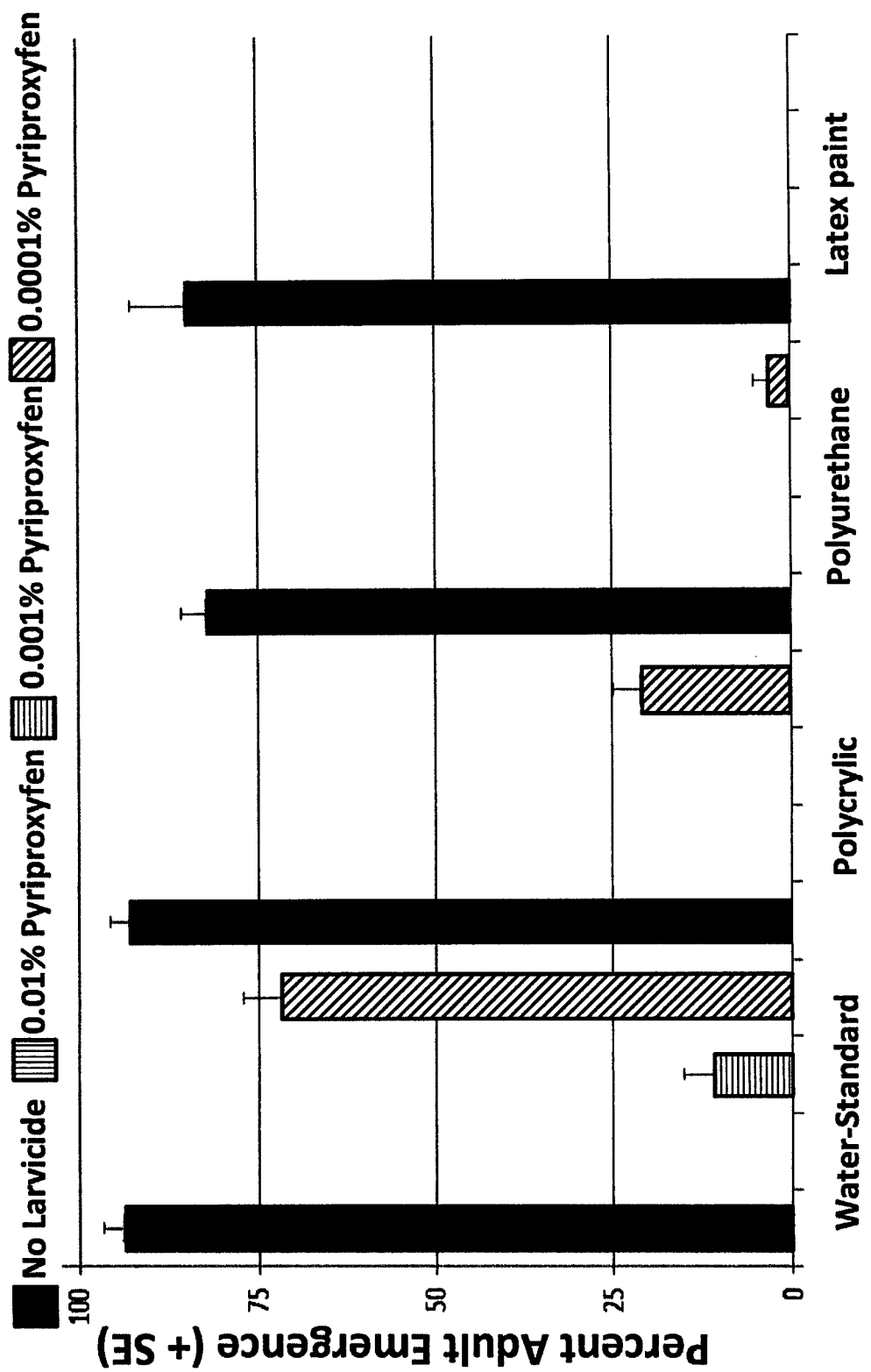
FIG. 23 shows percent adult mosquito emergence on the vertical axis versus coatings in which the larvicide pyriproxyfen was embedded at different rates.
Figure 24:
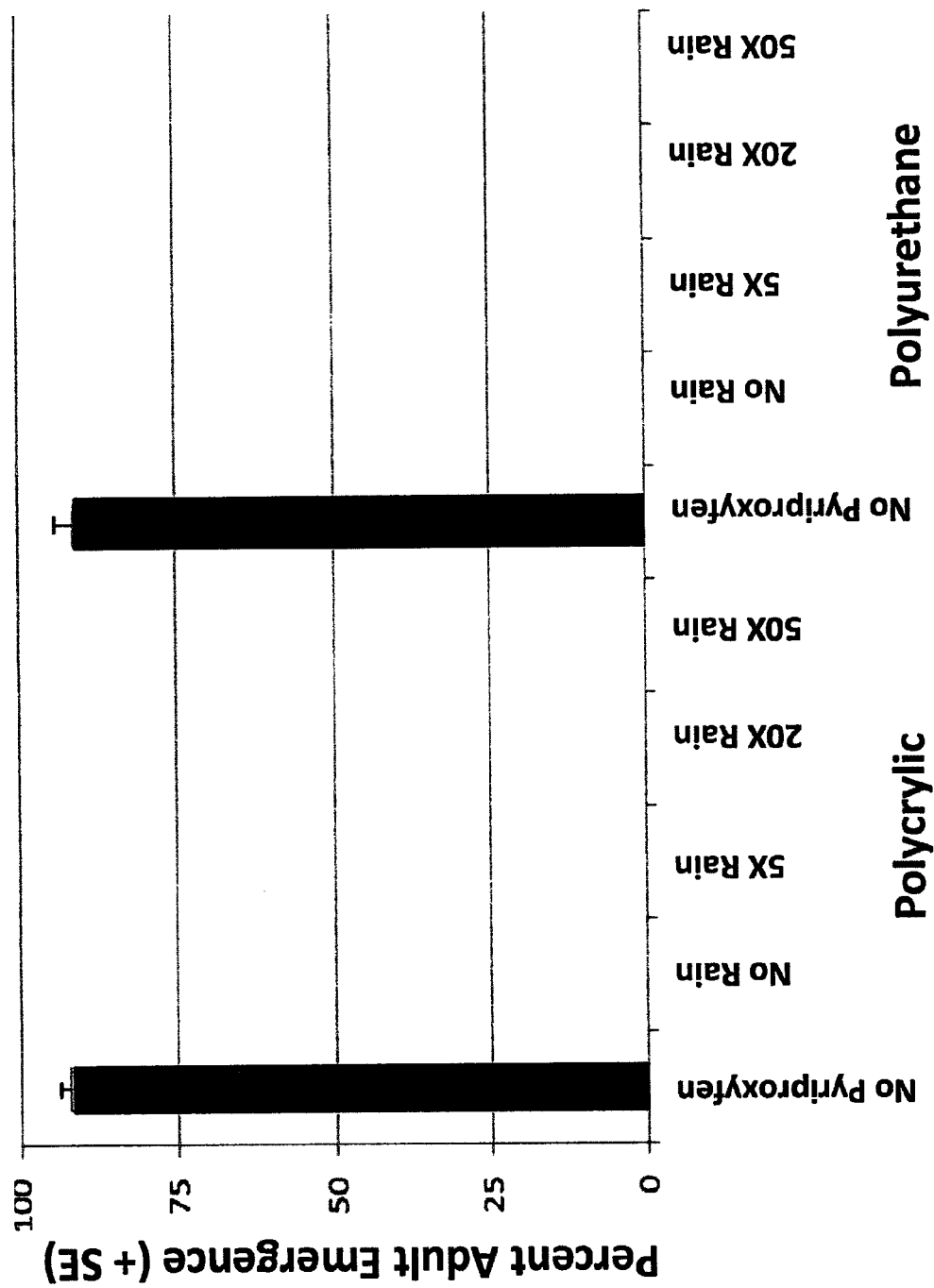
FIG. 24 shows percent adult mosquito emergence on the vertical axis versus two coatings in which the larvicide pyriproxyfen was embedded and applied to containers which were washed with different volumes of water.

FIG. 23 shows percent adult mosquito emergence on the vertical axis versus coatings in which the larvicide pyriproxyfen was embedded at different rates. FIG. 24 shows percent adult mosquito emergence on the vertical axis versus two coatings in which the larvicide pyriproxyfen was embedded and applied to containers which were washed with different volumes of water.

Referring to FIGS. 17-18, the placement of the larvicide pyriproxyfen in a coating does not prevent its action in preventing mosquito emergence, either with new material or material that had been aged for 20 weeks. In water that is in contact with the coating-embedded larvicide, or larvicide applied directly to the container without coating, mosquito larvae start to die as they reach the pupal stage. This shows that the coating does not interfere with the larvicide action. By embedding the larvicide pyriproxyfen in a coating, the mosquito killing action is protected from degradation for more than 20 weeks.

Referring to FIG. 19, mosquitoes (*Aedes aegyptii* and *Aedes albopictus*) preferred to lay eggs in cavities of 250 μm size, whereas smaller and larger cavities were not as preferred, and very large cavities (2000 µm) were even less preferred. This figure shows that a certain texture to the coating or container walls can make it a preferred oviposition site.

Referring to FIGS. 20-22, female mosquitoes were placed in cages where they had a choice of 2 containers filled with water to stimulate oviposition, one container with a coating-embedded adulticide (CEA) containing the adulticide permethrin, and the other container containing no insecticide. Reference to FIG. 20, pure water was used, whereas reference to FIG. 21, the water was mixed with oak-leaf infusion. In both tests, higher numbers of dead mosquito females were found in the adulticide-containing water, whereas greater number of eggs were found in containers with no insecticide. The presence of leaf infusion did not prevent the insecticidal action of the coating-embedded adulticide.

Referring to FIG. 22, adult female mosquitoes were found dead mostly in the container coated with coating-embedded adulticide, whereas few mosquitoes were found dead in the water-only control or the cage floor. This shows that once the adults contact the coating-embedded adulticide, they normally do not leave the container and die. Few mosquitoes that are able to fly away from the container with the coating-embedded adulticide also die later.

Referring to FIG. 23, three different coating were used to embed the larvicide pyriproxyfen at 3 different rates. Coatings were applied to plastic containers that were filled with water, before mosquito larvae were transferred to these containers. The addition of pyriproxyfen to different coatings produced similar results (no emergence of mosquitoes even at low pyriproxyfen content) while in the water standard, mosquito emergence was only inhibited at the high pyriproxyfen level. This shows that the different coatings can protect the action of pyriproxyfen.

Several different formulae (polycrylic, Polyurethane and Latex paint) have been tested as coatings for the larvicide. All coatings performed well in preventing adult emergence from larvae added to water-holding containers coated internally with the coating-embedded larvicide even with 0.0001% of the active ingredient in the coating. Water treated with 0.01% rate is considered potable by the World Health Organization (WHO).

Referring to FIG. 24, two of the coating tested previously (refer to FIG. 23) were also tested for durability under high volume washing to see if they could stand under heavy rains. The coatings applied to plastic containers were subject to continuous washing with tap water for total volumes equivalent to 5×, 20×, and 50× the container volumes. Afterwards the containers were refilled with fresh water and mosquito larvae were added to the water. Adult emergence from the larvae was only observed in containers with coatings that contained no embedded larvicide. The larvicide embedded in both coatings prevented the emergence of adults, even when the coating was washed with 50× volume of water. Coatings prevent larvicide washing off, with up to 50 times the volume of water as contained in the ovitrap. Most larvicides are applied to water and disappear when containers are emptied and refilled either naturally by rain action or by other means. The coating constantly treats new water put in containers with enough larvicide to preserve the mosquito-killing action. Both polycrylic and polyurethane protect the action of pyriproxyfen larvicide when containers coated with these materials are subjected to washing. This shows that coating-embedded larvicide can survive extensive rain-water rinsing.

The addition of larvicide kills any larvae that can emerge from eggs that females are able to lay before dying from exposure to adulticide in the lethal ovitrap. Field deployment of single-action lethal ovitrap allowed development of larvae which can lead to actual increase in the mosquito population.

As previously described, the invention can use drop-in objects having surfaces treated with polymer coatings having imbedded pesticides, that can be used to treat for mosquitoes in containers that can be exposed to water.

The types of objects that can be treated with imbedded pesticides can include but is not limited to chips, tokens, pebbles, stones and marbles.

Additionally, the types of objects that can be treated with imbedded pesticides can include but are not limited to ceramics, such as but not limited to small bathroom tiles, flooring tiles and wall tiles, and the like.

Additionally, the types of objects that can be treated with imbedded pesticides can include but are not limited to plastics, such as but not limited to acrylics, high-density polyethylene (HDPE), polypropylene and polycarbonate, and the like.

Additionally, the types of objects that can be treated with imbedded pesticides can include but are not limited to woods, such as but not limited to softwood, hardwood, and the like.

Table 4 lists the various dimensions of the objects that can be treated with imbedded pesticides.

TABLE 4

OBJECT/CHIP DIMENSIONS

| Thickness/Diameter | Broad Range | Narrow Range |
| --- | --- | --- |
| Thickness | Approx. 0.0001 in. to Approx. 2.0 in. | Approx. 0.03 in. to Approx. 0.2 in. |
| Diameter | Approx. 0.5 in. to Approx. 3 in. | Approx. 0.75 in. to Approx. 2.0 in. |

The object surfaces to be treated with imbedded pesticides can include flat and rough surfaces, and combinations thereof.

Table 5 lists the dimensions of the polymer coating layers with imbedded pesticides that can be applied to the surfaces of the objects.

TABLE 5

POLYMER LAYER DIMENSIONS

| Thickness/Diameter | Broad Range | Narrow Range |
| --- | --- | --- |
| Thickness | Approx. 0.001 in. to Approx. 0.125 in. | Approx. 0.01 in. to Approx. 0.1 in. |
| Diameter | Approx. 0.5 in. to Approx. 3 in. | Approx. 0.75 in. to Approx. 2.0 in. |

The polymer coatings with imbedded pesticides can be applied to the objects using techniques, such as but not limited to being applied as a spray, pipette on, painted on, spread on, and/or by dipping the objects in the polymer embedded pesticide coatings.

The coating can be applied under ambient (room temperature) and dry under ambient temperature in less than approximately five minutes.

The treated objects can be dropped into natural and/or manmade vessels, that are already filled with water or have no water at the time the objects are dropped in, so that water applied to the vessels by nature or by man allows for the water to be treated by the objects coated with the pesticide imbedded coatings.

The number of objects used per volume of water to be treated can range from 1 object per approximately 0.01 liters of water, up to approximately 1 object per approximately 200 liters of water to be treated.

The lifespans of the drop-in objects can broadly range between approximately 1 week to approximately 1 year. A narrower lifespan of the drop-in objects can range between approximately 1 week to approximately 6 months.

Once the lifespan is over the objects can be removed and discarded.

The components of the coating with imbedded pesticides that can be used are shown in Tables 6 to 10.

TABLE 6

Coating with Imbedded Pesticide Example

| Chemical | CAS# | Preferred Amnt % (approx.) | Broad Range % Approx. to Approx. | Narrow Range % Approx. to Approx. |
|---|---|---|---|---|
| Pyriproxyfen | 95737-68-1 | 1.00% | 10.0 to 0.005 | 2.0 to 0.5 |
| Fumed Silica | 7631-86-9 | 1.00% | 5.0 to 0.1 | 1.5 to 0.5 |
| Polymer (Iso-buthyl-methacrylate) | 9011-15-8 | 5.00% | 7.0 to 1.0 | 7.0 to 1.0 |
| Acetone | 67-64-1 | 93.0% | 87.0 to 98.895 | 87.0 to 98.895 |

Table 7 lists the types of synergists and their ranges and preferred amounts that can be used in the coatings with the imbedded pesticides. The insecticide formulation can include a synergist to overcome resistance in selected populations of insects. For example, an existing population of insects that were previously treated may have developed a resistance to insecticides. The synergist helps overcome that resistance.

TABLE 7

SYNERGISTS AND AMOUNTS

| SYNERGIST | RANGE % Approx. to Approx. | PREFERRED % Approximately |
|---|---|---|
| Piperonyl Butoxide | 0 to 10.0 | 0.7 |
| MGK-264 | 0 to 10.0 | 1.4 |
| Etofenprox | 0 to 5.0 | 0.7 |
| Pyrethrins | 0 to 5.0 | 0.7 |

MGK-264 refers to a common synthetic synergist used in insecticides. ETOFENPROX refers to another chemical name of a known synthetic synergist. PYRETHRINS refers to natural chemicals extracted from the flower *chrysanthemum*.

Table 8 lists the types of solvents and their ranges and preferred amounts that can be used in the coatings with the imbedded pesticides. The solvents can be used to dissolve the pesticide/insecticide and the polymer coating, so that the pesticide/insecticide is released over time.

TABLE 8

SOLVENTS AND AMOUNTS

| SOLVENTS | RANGE % Approx. to Approx. | PREFERRED % Approx. |
|---|---|---|
| Methanol | 87.0 to 98.895 | 93.0 |
| Ethanol | 87.0 to 98.895 | 93.0 |
| Acetone | 87.0 to 98.895 | 93.0 |
| Ethyl Acetate | 87.0 to 98.895 | 93.0 |
| Other organic Solvents | 87.0 to 98.895 | 93.0 |

Table 9 lists the types of pesticides and their ranges and preferred amounts that can be used in the coatings with the imbedded pesticides. Pyrofproxyfen would be a preferred pesticide to be used.

TABLE 9

PESTICIDES AND AMOUNTS

| PESTICIDE | RANGE % Approx. to Approx. | PREFERRED AMNT % Approx. |
|---|---|---|
| *Bacillus thuringiensis israelensis* | 0.0001 to 2 | 1.0 |
| Methoprene | 0.0001 to 2 | 1.0 |
| Pyroproxyfen | 0.0001 to 2 | 1.0 |
| Spinosad | 0.0001 to 2 | 1.0 |

Table 10 lists the types of plant oils and their ranges and preferred amounts that can be used in the coatings with the imbedded pesticides. Plant oils are known repellants and can be used as a substitute or in combination with pesticides/insecticides that require direct contact with insects. The plant oil can be used instead of insecticides on the strips and/or chips, to repel mosquitoes from laying eggs in water, and can be advantageous for use in drinking water supplies. Another use would be having strips and/or chips with plant oil, and separate strips and/or chips with the insecticide for use about surfaces that come in contact with water.

TABLE 10

PLANT OILS AND AMOUNTS

| PLANT OILS | RANGE % Approx. to Approx. | PREFERRED % Approximately |
|---|---|---|
| Tea tree | 0.0001 to 2 | 1.0 |
| Geraniol | 0.0001 to 2 | 1.0 |
| Citronella | 0.0001 to 2 | 1.0 |
| Clove Oil | 0.0001 to 2 | 1.0 |

Peel and Stick Embodiments

Peel and stick tape type material can be used to adhere one or more objects coated with pesticide imbedded coatings, such as those previously described.

The types of peel and stick materials, can include but are not limited to off-the shelf materials, such as but not limited to bathtub non-strip stickers, bathtub non-strips, anti-skid tread tape, and the like.

The material that can be used can include but is not limited to rubber, natural and synthetic fibers (such as nylon fibers, plastic, fibers, and the like), cloth, sandpaper, cellulose, combinations thereof, and the like.

In a preferred embodiment, the peel and stick can include three layers of material, that include an adhesive, peelable backing layer, and peelable cover layer.

The adhesive, can be a long lasting, water resistant adhesive. The backing material, can be paper, cellulose. The peelable cover material, can be a clear plastic.

Off the shelf products that can be used can include Moen Home Care, Tread Strips, and Shurtape, Anti-Skid Tread Tape.

The peel and stick embodiments can be applied in natural and manmade vessels that can contain water or can come in contact with water.

Instructions for using the peel and stick applications can include the following steps:

1. Clean surface where peel and stick mosquitocidal chip (PSMC) will be affixed to.
2. Remove backing from PSMC.

3. Place PSMC in the container/vessel at a position where it will be constantly submersed in water, and press the glue side against the container wall.
4. Make sure PSMC is secure in place before adding water to the container.
5. Peel off the protective plastic covering and discard it in the trash.

Table 11 provides dimensions for a peel and stick patch that can have a circular configuration

TABLE 11

PEEL AND STICK PATCH DIMENSIONS

| Patch | Broad Range | Narrow Range |
| --- | --- | --- |
| Thickness | Approx. 0.001 in. to Approx. 0.125 in | Approx. 0.01 in. Approx. 0.1 in. |
| Diameter | Approx. 0.5 in. to Approx. 3 in. | Approx. 0.75 in. Approx. 2.0 in. |

The peel and stick patches can provide in singular locations and/or in a plurality of locations within a vessel that can hold water, such as but not limited to those previously described.

FIG. 25A shows a roll 1200 of treated peel and stick mosquitocidal chip (PSMC), perforations separating sections 1210. The user can tear off a rectangular section 1210 when ready to be used.

A separated section 1210 can include a removable adhesive-protective layer 1211 that exposes an adhesive surface to the backing layer 1212, such as a flexible material and that can include but is not limited to paper layer (with or without a water-proof treatment (silicon coated and the like), plastic layer, cloth layer (such as synthetic fibers), rubber layer, combinations thereof, and the like. 1213 can include the polymer layer coating applied to the top of the backing layer 1212. The polymer layer can include imbedded silica and pesticide. An outer peelable layer can be applied on top the polymer layer with imbedded silica and pesticide.

The rolls can have lengths from inches to yards with widths of up to several inches (such as up to approximately 3 inches or more). The section can have a thickness of approximately 1 mm up to approximately 5 mm and larger.

Figure 25B:
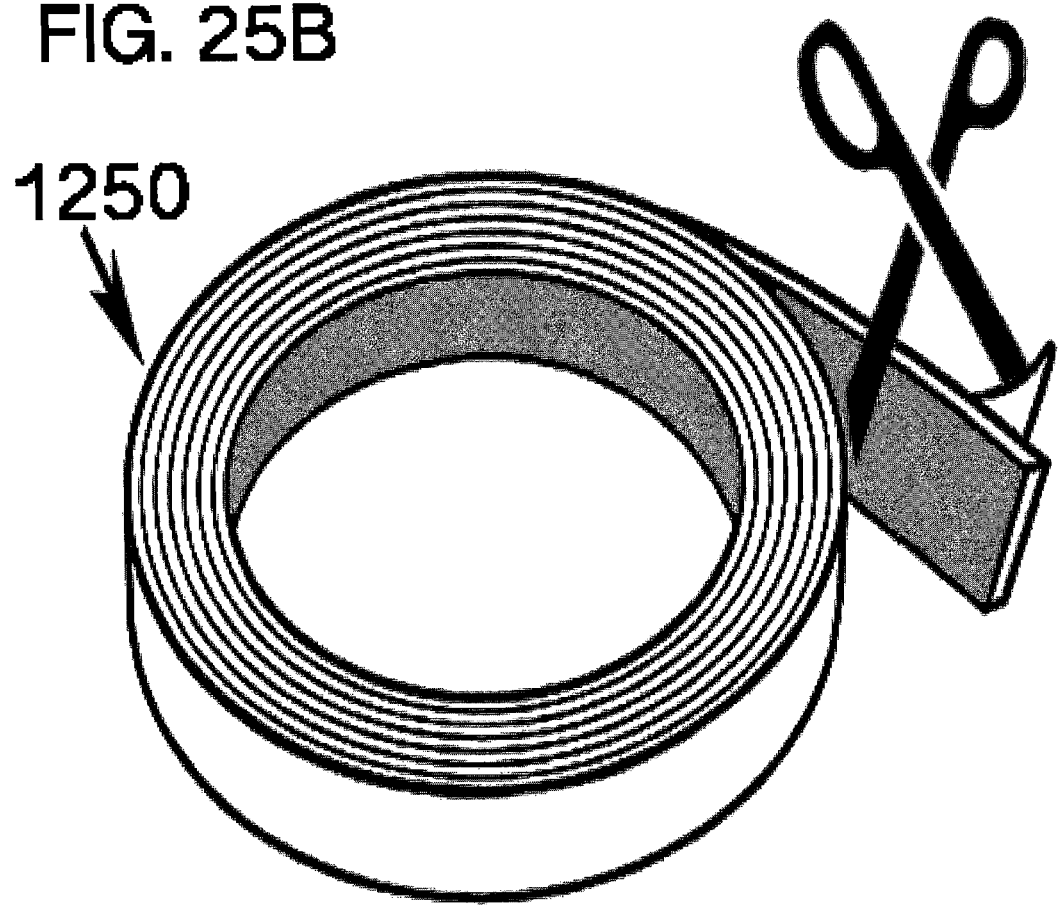
FIG. 25B shows another roll of treated peel and stick having mosquitocidal chips (PSMC) with sections that can be cut so that different size sections can be used.

FIG. 25B shows a continuous roll 1250 of treated peel and stick having mosquitocidal chips (PSMC) with sections that can be cut so that different size sections can be used. The user can cut the desired length of each section, so that one or more sections, each with chip type objects can be applied to surfaces needing treatment.

Figure 26A:
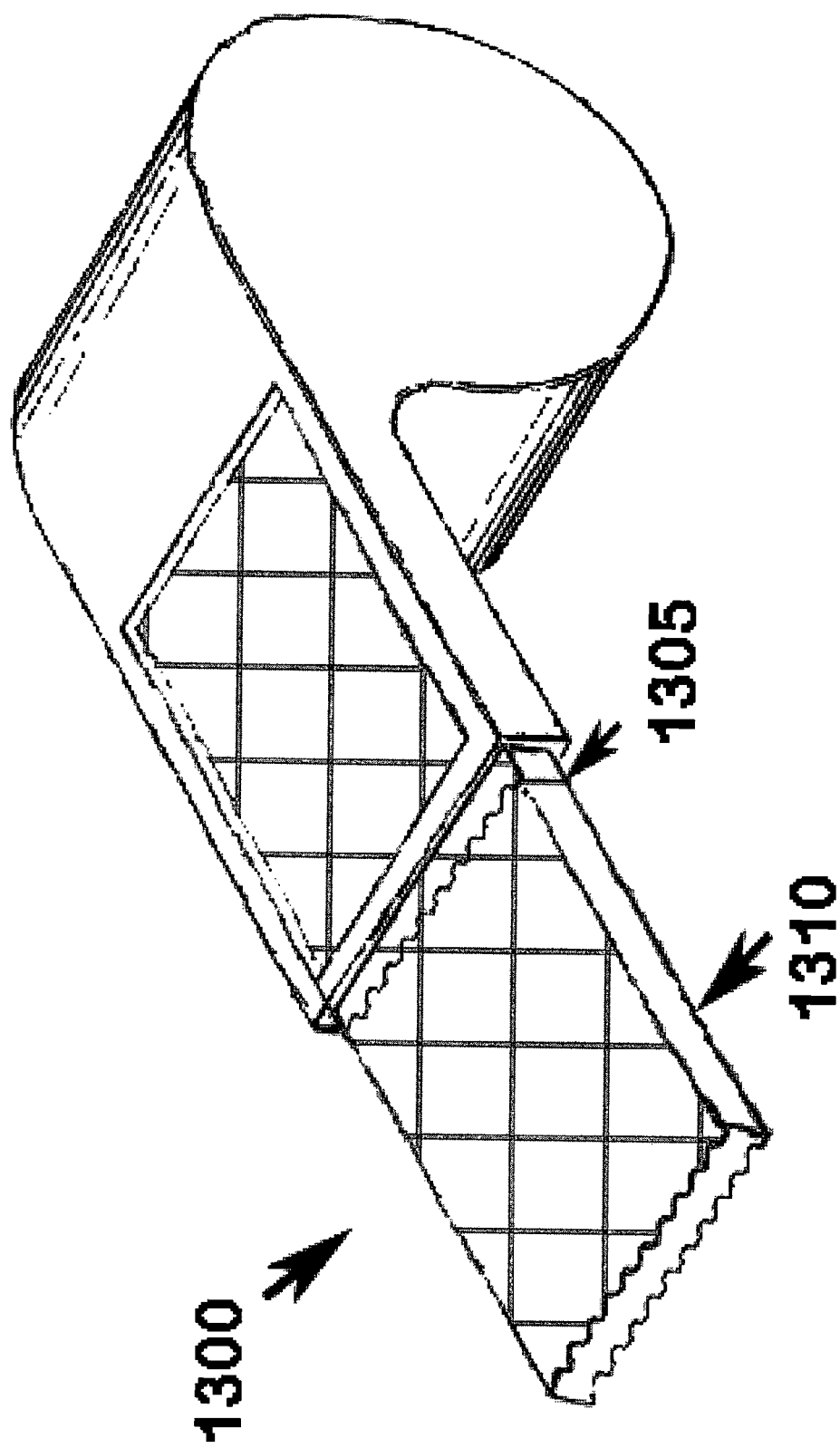
FIG. 26A shows a dispenser for a roll of treated peel and stick having mosquitocidal chips (PSMC), with a cutting edge.
Figure 26B:
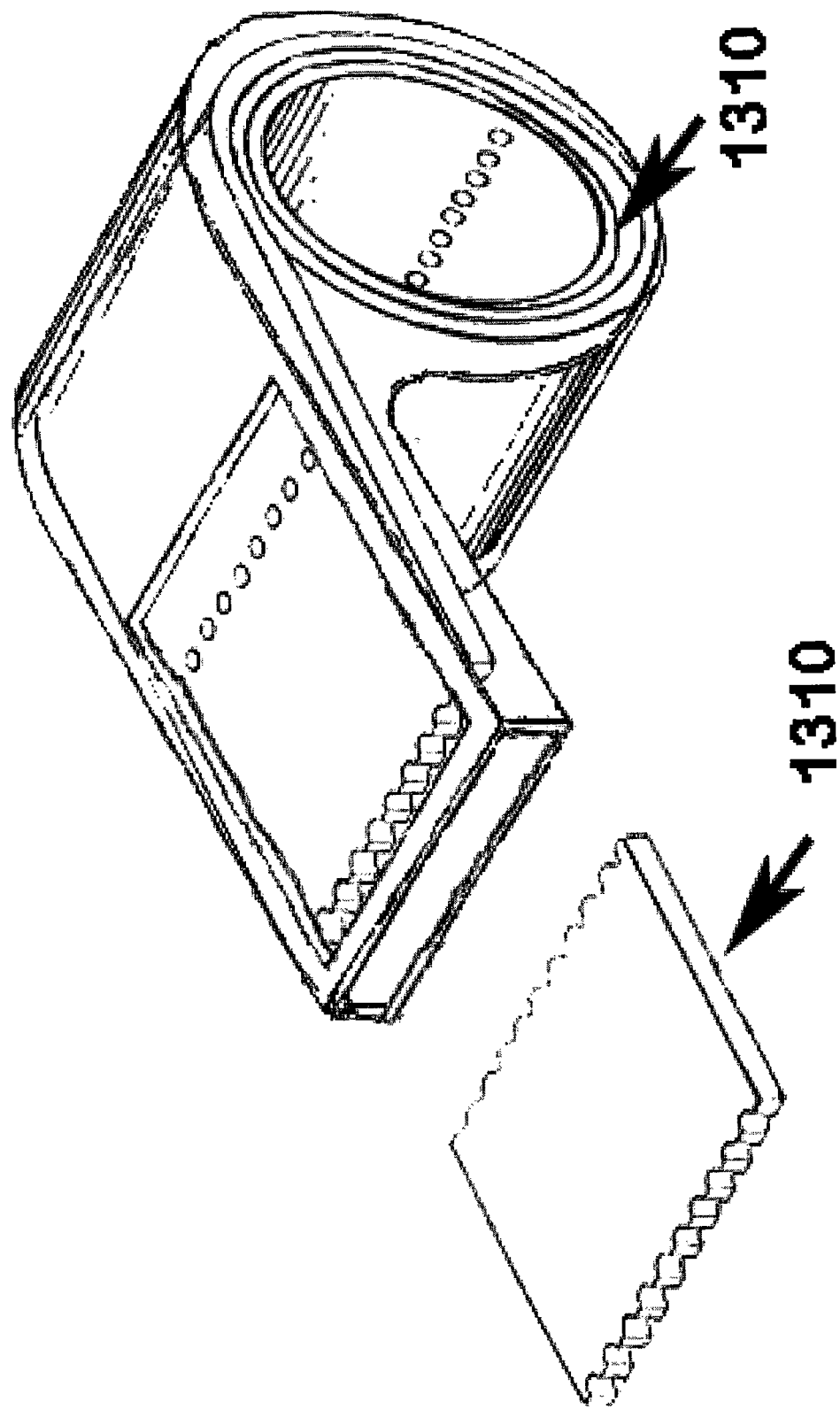
FIG. 26B is a cross-sectional view of the dispenser of FIG. 26A.

FIG. 26A shows a dispenser 1300 for a roll 1310 of treated peel and stick having mosquitocidal chips (PSMC), with a cutting edge 1305. FIG. 26B is a cross-sectional view of the dispenser 1300 of FIG. 26A. The user can pull an outer edge from the roll 1310 in side of the dispenser 1300 and tear off a selected length by ripping against the cutting edge 1305.

Figure 27:
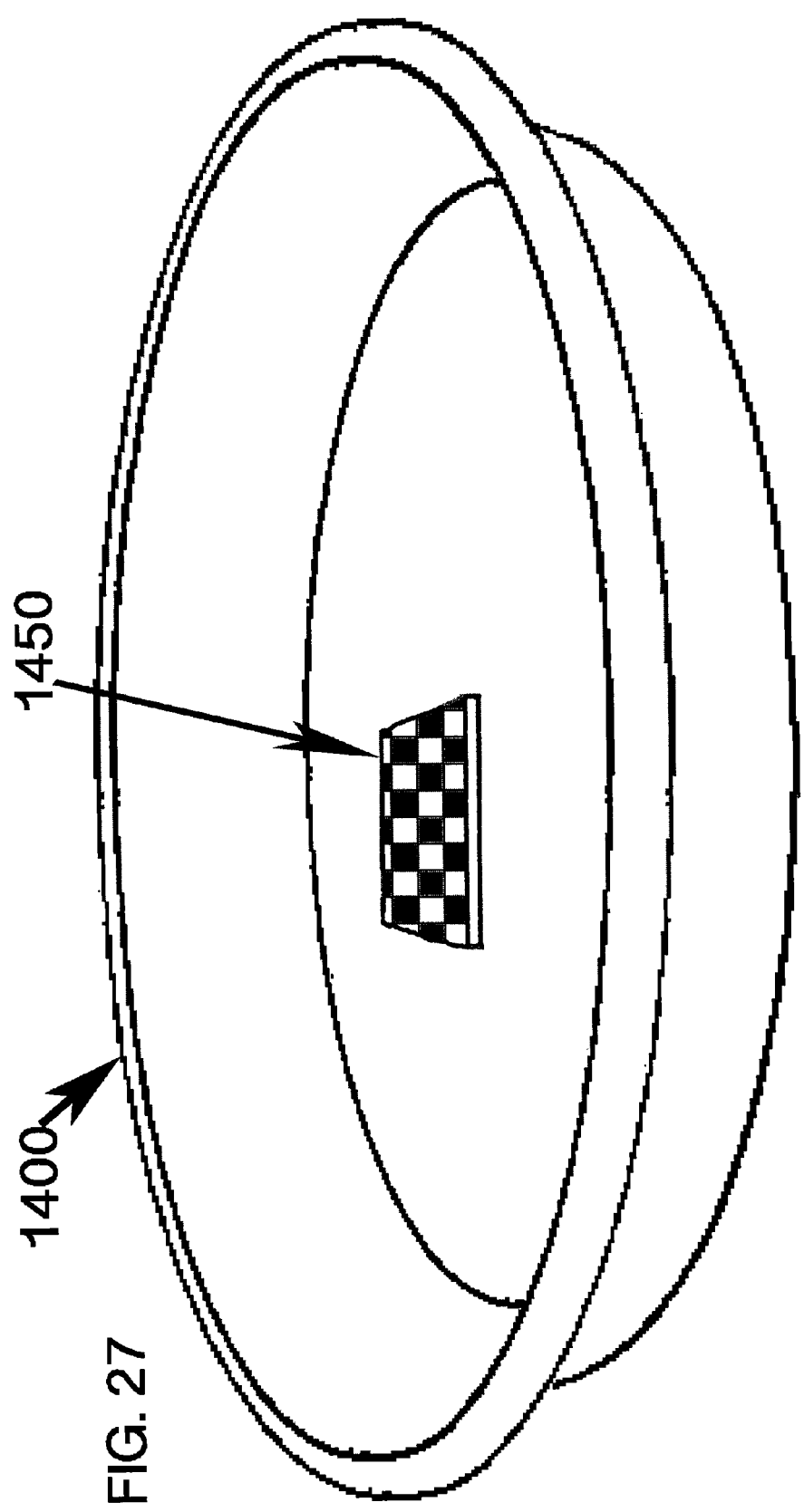
FIG. 27 shows a top view of a vessel, such as a container, that can hold water with a peel and stick patch/section.

FIG. 27 shows a top view of a vessel 1400 that can hold water with a peel and stick patch/section 1450 attached to an inside surface such as on the bottom and/or on the inner side of the vessel. The vessel 1400 can be manmade such as any of containers, and the like, such as those previously shown and described.

The lifespan of the peel and stick patches/strips can range from approximately 1 week to approximately 1 year, and more narrowly between approximately 1 to approximately 6 months.

A preferred list of instructions for using the peel and stick mosquitocidal chip (PSMC) can include:

1. Clean the surface where the peel and stick mosquitocidal chip (PSMC) will be affixed to.
2. Remove the backing from the PSMC
3. Place the PSMC in the vessel such as a container at a position where it will be constantly submersed in water, and press the exposed adhesive side against the container wall.
4. Make sure PSMC is secure in place before adding water to the container.
5. Peel off the protective plastic covering and discard it in the trash.

FIG. 28 is an enlarged side cross-sectional view of a single section/patch of a treated peel and stick having mosquitocidal chips (PSMC).

FIG. 29 is an enlarged cross-sectional view of FIG. 28 with the upper and lower protective surface layers removed.

FIG. 30 is an enlarged cross-sectional view of FIG. 29 with the adhesive lower surface attached to a base surface such but not limited to the inner side and/or bottom of a vessel that can hold water.

Referring to FIGS. 28-30, backing layer 1, can include but is not limited to paper layer (with or without a water-proof treatment (silicon coated and the like), plastic layer, cloth layer (such as synthetic fibers), rubber layer, combinations thereof, and the like. The polymer coating 2 applied to the top of the backing layer 1, can be a polymer coating 2 imbedded with insecticide 4 and silica particles 3 (such as silica powder, and the like).

A removable insecticide-protective layer 7, can include but not be limited to paper, plastic, and the like can be removed to expose the polymer coating 2 imbedded with insecticide 4 and silica particles 3. On the bottom of the backing layer 1 can be a water-resistant adhesive layer 5 which is covered by a removable adhesive-protective layer 6, which when removed allows the backing layer 1 to be attached to the surface of the container or vessel that can hold water being treated.

FIG. 31 shows a flat strip 1600 of individual peel and stick chip type discs 1610 which are separated from a removable adhesive-protection tape.

FIG. 32 shows one of the peel and stick chip type discs of FIG. 31 with the adhesive protection tape removed, now ready to be applied to a support surface.

Referring to FIGS. 31-32, the chip disc 1610 can have an upper surface with a polymer coating layer 1620 having imbedded silica and insecticide, with a peel and stick layer protecting the coating with imbedded silica and insecticide. Underneath the chip disc 1610 can be an adhesive layer 1630, covered by a removable adhesive protective tape 1640.

The peel and stick embodiments can apply the tape with polymer coating and imbedded pesticide with or without silica, as well as the chip(s) with polymer coating and imbedded pesticide and silica, to any surface (side wall, floor type surface, any surface underwater, and the like) that would come in contact with water. The surfaces can include containers, vessels, manmade surfaces (tiles, bricks, metal surfaces, plastic surfaces, and the like), and natural surfaces (rocks, trees, plants, and the like), and the like.

The tape and chip applications can be adhered to surfaces that become in contact with water. The surfaces can be initially dry or wet. The tape and chip applications can work in surfaces that are either wet or become submerged under water.

The term "approximately" can be +/−10% of the amount referenced. Additionally, preferred amounts and ranges can include the amounts and ranges referenced without the prefix of being approximately.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method of applying mosquito pesticide coated objects into water holding areas, comprising the steps of:
   providing a polymer coating with an imbedded pesticide, the pesticide comprising at least a larvicide which directly kills mosquito larvae over time;
   applying the polymer coating with the imbedded pesticide to a surface on a side of a strip;
   exposing an adhesive surface on another side of the strip; and
   applying the adhesive surface of the strip against a surface that is exposed to water; and
   leaching out the larvicide into the water to treat and directly kill the mosquito larvae over time.

2. The method of claim 1, wherein the strip is selected from paper, plastic, cloth and rubber.

3. The method of claim 1, further comprising the step of:
   providing a lower removable protective layer for covering the adhesive surface, wherein removing the lower protective layer allows for the strip to adhered to the surface.

4. The method of claim 3, further comprising the step of:
   providing an upper removable protective layer for covering the insecticide surface, wherein removing the upper protective layer allows for releasing the insecticide.

5. The method of claim 1, wherein the surface is selected from the group consisting of containers, aquariums, flower pots, water holding dishes used under plant pots, vases, bird baths, and fountains and storm water inlets.

6. The method of claim 1, wherein the pesticide further includes:
   an adulticidal coating with the larvicidal coating, which together kills both adult mosquitoes and their larvae over time.

7. A peel and stick pesticide-coated treatment device to kill mosquitoes, comprising:
   a strip treated with a polymer coating having a pesticide embedded in the coating, the pesticide comprising at least a larvicide which directly kills mosquito larvae over time;
   an adhesive surface on the strip; and
   a lower protective layer covering the adhesive surface, wherein removing the protective layer allows the strip to be applied to a water exposed surface for directly treating mosquito larvae over time.

8. The peel and stick pesticide coated treatment device of claim 7, wherein the strip includes:
   a patch.

9. The peel and stick pesticide coated treatment device of claim 7, wherein the strip includes:
   a roll of strips.

10. The peel and stick pesticide treatment device of claim 9, wherein the roll of strips includes: perforations for separating a plurality of strips from one another.

11. The peel and stick pesticide coated treatment device of claim 9, further comprising:
    a dispenser for housing the roll of strips.

12. The peel and stick pesticide coated treatment device of claim 11, wherein the dispenser includes:
    a cutting edge for allowing a section of the roll to be torn off.

13. The peel and stick pesticide coated treatment device of claim 9, wherein the strip includes:
    a top protective layer for protecting the coating having the pesticide, the top layer being removed to allow the pesticide to be released.

14. The peel and stick pesticide coated treatment device of claim 7, wherein the pesticide further includes:
    an adulticide with the larvicide which together kills both adult mosquitoes and their larvae over time.

15. A peel and stick pesticide coated treatment device, comprising:
    a plurality of chips, each chip having an upper surface with a polymer coating imbedded with a pesticide and silica, the pesticide comprising at least a larvicide which directly kills mosquito larvae over time;
    an adhesive surface on a lower surface of each chip, wherein the adhesive surface allows for the chip to be adhered to a water exposed surface for treatment against mosquito larvae.

16. The peel and stick pesticide of claim 15, wherein each chip further comprises:
    a removable upper protective layer for protecting the polymer coating imbedded with the pesticide and silica; and
    a removable lower protective layer for protecting the adhesive surface.

17. The peel and stick pesticide of claim 16, wherein the removable lower protective layer includes:
    a single elongated strip forming the removable lower protective layer for the plurality of chips.

18. A peel and stick pesticide coated treatment device of claim 15, wherein the pesticide further includes:
    an adulticide with the larvicide which together kills both adult mosquitoes and their larvae over time.

* * * * *

UNITED STATES PATENT AND TRADEMARK OFFICE
CERTIFICATE OF CORRECTION

PATENT NO. : 9,775,335 B2
APPLICATION NO. : 15/367874
DATED : October 3, 2017
INVENTOR(S) : Philip G. Koehler, Roberto M. Pereira and Enrico Paolo Levi It is certified that error appears in the above-identified patent and that said Letters Patent is hereby corrected as shown below:

In the Specification

Column 1, Line 20 under Government License Rights, the following should be included:
The invention was made with government support under Cooperative Agreement 58-0208-3-001 awarded by the United States Department of Agriculture. The government has certain rights in the invention.

Signed and Sealed this
Twenty-second Day of May, 2018

Andrei Iancu
*Director of the United States Patent and Trademark Office*